(12) United States Patent
Moriyama et al.

(10) Patent No.: US 7,345,292 B2
(45) Date of Patent: *Mar. 18, 2008

(54) PARTICLE BEAM THERAPY SYSTEM

(75) Inventors: Kunio Moriyama, Hitachi (JP); Akihiko Maeda, Hitachi (JP); Yoshikatsu Yasue, Tokyo (JP); Takahide Nakayama, Nara (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/327,343

(22) Filed: Jan. 9, 2006

(65) Prior Publication Data

US 2006/0118736 A1  Jun. 8, 2006

Related U.S. Application Data

(63) Continuation of application No. 10/790,850, filed on Mar. 3, 2004, now Pat. No. 7,012,267.

(30) Foreign Application Priority Data

Mar. 7, 2003 (JP) .............................. 2003-062585

(51) Int. Cl.
*A61N 5/10* (2006.01)

(52) U.S. Cl. ................. 250/492.3; 250/398; 250/492.1

(58) Field of Classification Search .............. 250/492.3

See application file for complete search history.

(56) References Cited

U.S. PATENT DOCUMENTS

| | | | |
|---|---|---|---|
| 4,870,287 A | 9/1989 | Cole et al. | |
| 5,260,581 A | 11/1993 | Lesyna et al. | |
| 5,585,642 A | 12/1996 | Britton et al. | |
| 5,895,926 A | 4/1999 | Britton et al. | |
| 6,580,084 B1 | 6/2003 | Hiramoto et al. | |
| 7,012,267 B2 * | 3/2006 | Moriyama et al. | 250/492.3 |
| 2001/0022502 A1 | 9/2001 | Akiyama et al. | |
| 2004/0173763 A1 * | 9/2004 | Moriyama et al. | 250/492.1 |
| 2004/0174958 A1 * | 9/2004 | Moriyama et al. | 378/145 |
| 2004/0183033 A1 | 9/2004 | Moriyama et al. | |
| 2004/0200982 A1 * | 10/2004 | Moriyama et al. | 250/492.3 |
| 2006/0022152 A1 * | 2/2006 | Natori et al. | 250/493.1 |

(Continued)

FOREIGN PATENT DOCUMENTS

JP  U-5-35154  5/1993

(Continued)

*Primary Examiner*—Nikita Wells
*Assistant Examiner*—James J Leybourne
(74) *Attorney, Agent, or Firm*—Dickstein Shapiro LLP

(57) ABSTRACT

A first manual input device for inputting an irradiation ready state is provided in each treatment room or a control room formed corresponding to the treatment room. A safety device confirms that preparations for generation of an ion beam in an accelerator are completed and preparations for transport of the ion beam in a beam transport system for introducing the ion beam to an irradiation unit in the treatment room selected in response to a ready signal from the first manual input device are completed, followed by outputting ready information. A ready state display unit for displaying the ready information is provided. In the treatment room or the control room, a second manual input device is provided for inputting an irradiation start instruction when the ready information is displayed by the ready state display unit.

4 Claims, 19 Drawing Sheets

U.S. PATENT DOCUMENTS

| | | | |
|---|---|---|---|
| 2006/0076515 A1* | 4/2006 | Matsuda et al. | 250/492.23 |
| 2006/0113487 A1* | 6/2006 | Naumann et al. | 250/492.3 |
| 2006/0118736 A1* | 6/2006 | Moriyama et al. | 250/493.1 |
| 2007/0018121 A1* | 1/2007 | Leyman et al. | 250/494.1 |

FOREIGN PATENT DOCUMENTS

| | | |
|---|---|---|
| JP | A-8-229145 | 9/1996 |
| JP | 11-501232 | 2/1999 |
| JP | A-11-197258 | 7/1999 |
| JP | 2001-85200 | 3/2001 |
| JP | A-2002-7822 | 1/2002 |
| JP | A-2002-91531 | 3/2002 |
| WO | WO 02/45793 A2 | 6/2002 |

* cited by examiner

FIG.7

PATIENT DATA

| PATIENT ID No. | DOSE | (TREATMENT ROOM No.) | ENERGY | ... |
|---|---|---|---|---|
| 650098 | ... | (No.1) | 70Mev | ... |

FIG.8

GB : BENDING ELECTROMAGNET
GQ : QUADRUPOLE ELECTROMAGNET

| ENERGY (MeV) | COMMON | | | | | | |
|---|---|---|---|---|---|---|---|
| | BEFORE ACCELERATION | | SYNCHROTRON | | | AFTER ACCELERATION | |
| | GB10 | GQ9 | GB14 | GQ13 | GQ13 | GB17 | GQ18 |
| 70 | | | Pattern 70 | | | ... | ... |
| 80 | ... | ... | Pattern 80 | | | ... | ... |
| 90 | | | Pattern 90 | | | ... | ... |
| ⋮ | ⋮ | ⋮ | ⋮ | ⋮ | ⋮ | ⋮ | ⋮ |

| ENERGY (MeV) | No.1 TREATMENT ROOM 2A | | No.1 to No.2 | No.2 TREATMENT ROOM 2B | | No.2 to No.3 | No.3 TREATMENT ROOM 2C | |
|---|---|---|---|---|---|---|---|---|
| | GQ22A | GQ24A | GQ19 | GQ22B | GQ24B | GQ20 | GQ22C | GQ24C |
| 70 | ... | ... | ... | ... | ... | ... | ... | ... |
| 80 | ... | ... | ... | ... | ... | ... | ... | ... |
| 90 | ... | ... | ... | ... | ... | ... | ... | ... |
| ⋮ | ⋮ | ⋮ | ⋮ | ⋮ | ⋮ | ⋮ | ⋮ | ⋮ |

| ENERGY (MeV) | No.3 to No.4 | No.4 TREATMENT ROOM 3 | SWITCHING POWER SOURCE 162-1 | SWITCHING POWER SOURCE 162-2 | SWITCHING POWER SOURCE 162-3 | SWITCHING POWER SOURCE 162-4 |
|---|---|---|---|---|---|---|
| | GQ27 | GQ28 | | | | |
| 70 | ... | ... | ... | ... | ... | ... |
| 80 | ... | ... | ... | ... | ... | ... |
| 90 | ... | ... | ... | ... | ... | ... |
| ⋮ | ⋮ | ⋮ | ⋮ | ⋮ | ⋮ | ⋮ |

FIG.9

GB : BENDING ELECTROMAGNET
GQ : QUADRUPOLE ELECTROMAGNET

| TREAT-MENT ROOM No. | COMMON | | | | | | |
|---|---|---|---|---|---|---|---|
| | BEFORE ACCELERATION | | SYNCHROTRON | | AFTER ACCELERATION | | |
| | GB10 | GQ9 | GB14 | GQ13 | GQ13 | GB17 | GQ18 |
| 1 | ON | | | | | | |
| 2 | | | | | | | |
| 3 | | | | | | | |
| 4 | | | | | | | |

| TREAT-MENT ROOM No. | No.1 TREATMENT ROOM 2A | | No.1 to No.2 | No.2 TREATMENT ROOM 2B | | No.2 to No.3 | No.3 TREATMENT ROOM 2C | |
|---|---|---|---|---|---|---|---|---|
| | GQ22A | GQ24A | GQ19 | GQ22B | GQ24B | GQ20 | GQ22C | GQ24C |
| 1 | ON | | No Care | | | | | |
| 2 | No Care | | ON | ON | | No Care | | |
| 3 | No Care | | ON | No Care | | ON | ON | |
| 4 | No Care | | ON | No Care | | ON | No Care | |

| TREAT-MENT ROOM No. | No.3 to No.4 | No.4 TREAT-MENT ROOM 3 | | SWITCHING POWER SOURCE 162-1 | SWITCHING POWER SOURCE 162-2 | SWITCHING POWER SOURCE 162-3 | SWITCHING POWER SOURCE 162-4 |
|---|---|---|---|---|---|---|---|
| | | GQ27 | GQ28 | | | | |
| 1 | | | | ON | | | |
| 2 | | | | | | | |
| 3 | No Care | | | | | | |
| 4 | ON | ON | | | | | |

FIG.12

| TREATMENT ROOM No. | SWITCH No. | | | | | | | |
|---|---|---|---|---|---|---|---|---|
| | 1 | 2 | 3 | 4 | 5 | 6 | 7 | 8 |
| 1 | 1 | 1 | 1 | 1 | 1 | 1 | 1 | 1 |
| 2 | 1 | 2 | 2 | 2 | 1 | 2 | 1 | 2 |
| 3 | 2 | No Care | 2 | No Care | 2 | No Care | 2 | No Care |
| 4 | No Care | No Care | No Care | No Care | No Care | No Care | No Care | No Care |

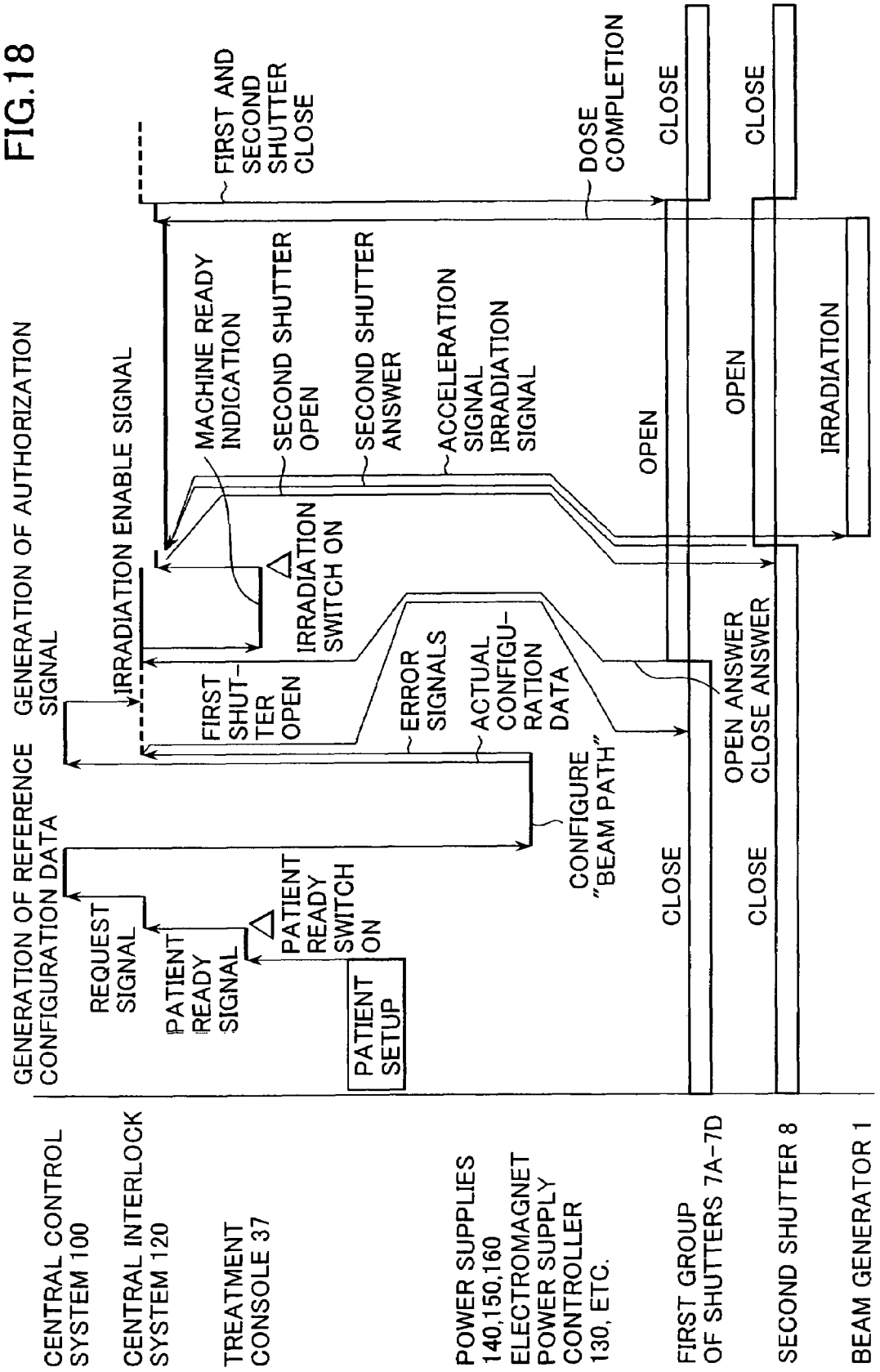

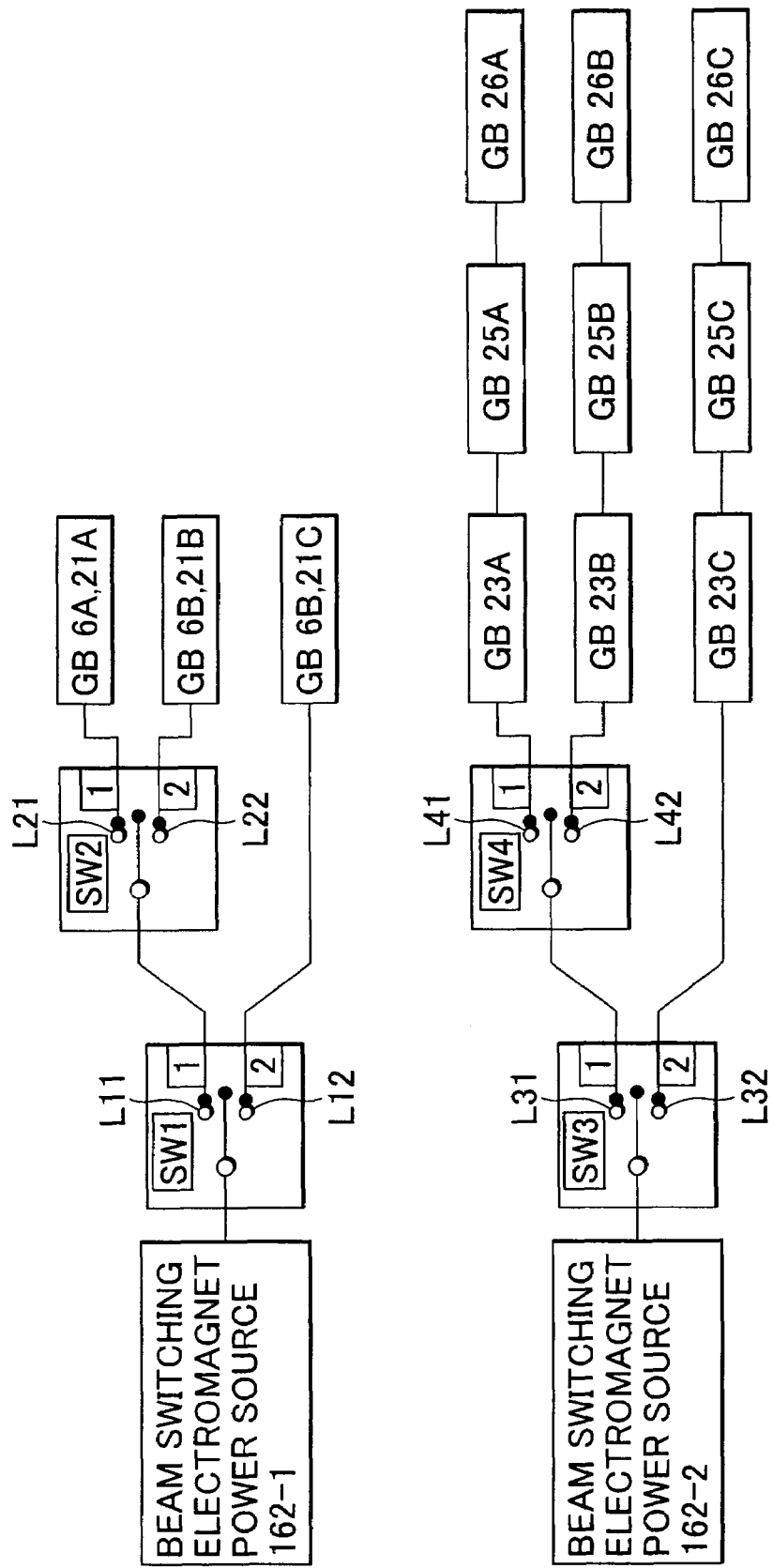

PARTICLE BEAM THERAPY SYSTEM

This is a continuation application of U.S. patent application Ser. No. 10/790,850, filed on Mar. 3, 2004 now U.S. Pat. No. 7,012,267, the entire disclosure of which is incorporated by reference herein.

BACKGROUND OF THE INVENTION

1. Field of the Invention

The present invention relates to a particle beam therapy system, and more particularly to a particle beam therapy system in which a charged particle beam, such as a proton or carbon ion beam, is irradiated to a diseased part (tumor) for treatment.

2. Description of the Related Art

There is known a therapy method of irradiating a beam of charged particles, such as protons, to a tumor, e.g., a cancer, in a patient's body. A large-scaled one of therapy systems for use with that therapy method comprises a charged particle beam generator, a beam transport system, and a plurality of treatment rooms. A charged particle beam accelerated by the charged particle beam generator reaches an irradiation unit in each of the treatment rooms through the beam transport system, and is irradiated to the tumor in the patient's body from a nozzle of the irradiation unit. In addition, the beam transport system comprises one common beam transport system and a plurality of branched beam transport systems which are branched from the one common beam transport system and extended into the respective irradiation units in the treatment rooms. At a position where each of the branched beam transport system is branched, a switching electromagnet is disposed which deflects the charged particle beam incoming from the one common beam transport system and introduces it into the corresponding branched beam transport system (see, e.g., Patent Reference; U.S. Pat. No. 5,585,642(JP,A 11-501232); from line 47, column 4 to line 34, column 5).

SUMMERY OF THE INVENTION

In the known particle beam therapy system described above, when performing irradiation treatment in each treatment room, the charged particle beam is selectively introduced from the one common beam transport system to only the relevant treatment room. At that occasion, all the switching electromagnets are controlled in accordance with control signals from a controller to switch over excitation such that a beam transport path (route) to the relevant treatment room is formed. With that control, the charged particle beam is prevented from being erroneously introduced to another treatment room different from one to which the charged particle beam is to be introduced in a normal state.

Considering the possibility that the controller may malfunction or cause an instable state in control for some reason, however, the above-mentioned process of merely forming the beam transport path by switching control of the electromagnet excitation in accordance with the control signals from the controller still has a room for improvement from a safety point of view in reliably preventing the beam from being erroneously transported to other treatment room than the irradiation target.

It is an object of the present invention to provide a particle beam therapy system in which treatment-using a charged particle beam can be performed on patients in a safe and prudent manner without problems.

To achieve the above object, a feature of the first invention resides in that, in at least one of a plurality of beam transport systems for transporting a charged particle beam emitted from a charged particle beam generator separately to respective irradiation units in a plurality of treatment rooms, a first shutter is provided to shut off a beam path in that one beam transport system. With the provision of the shutter in the beam path for physically blocking the beam itself, safety can be remarkably improved in comparison with the related art resorting to only reliability of software used in an electromagnet switching controller. For more remarkably improving safety, it is preferable to provide the first shutter to shut off each of the beam paths in all the beam transport systems.

A feature of the second invention resides in including a control information forming unit for forming control command information, which includes control information for a plurality of elements provided in the beam transport system introducing the charged particle beam to an irradiation unit in a selected treatment room, by using at least treatment room information representing the selected treatment room and treatment plan information specified depending on patient identification information for a patient who enters the selected treatment beam. With this feature, the system construction can be simplified and the treatment can be smoothly conducted at higher efficiency. More specifically, the doctor side is just required to prepare only the treatment plan information for each patient, and the operator side is just required to input only the patient identification information and the treatment room information, both representing who is present as the patient in which one of the treatment rooms, to the control information forming unit. Based on both the treatment plan information obtained depending on the patient identification information and the treatment room information, the control information forming unit automatically forms final control command information for operating the charged particle beam generator and switching electromagnets. As a result, when forming the control command information, it is no longer required to prepare a large amount of data covering all of the treatment plan information for each patient set from the medical point of view and the information necessary for operating the therapy system. Thus, since work for preparing data can be separately allocated to the doctor side and the operator side, the system construction can be simplified and the treatment can be smoothly conducted at higher efficiency.

A feature of the third invention resides in including a control system for deciding the sequence of introducing the charged particle beam to the plurality of treatment rooms based on respective irradiation ready signals corresponding to the treatment rooms, and forming the beam paths for introducing the charged particle beam, emitted from the charged particle beam generator, to the respective irradiation units in the treatment rooms in accordance with the decided sequence.

With that feature, the time and labor imposed on the operator can be reduced to a large extent. Practically, when making preparations for irradiation in one treatment room, it is possible to flexibly progress the preparations for irradiation with no need of taking into account situations in the other treatment rooms. In other words, unlike the case of presetting the irradiation sequence for the respective treatment rooms and transporting the beam in accordance with the preset sequence, the treatment room in which the preparations for irradiation are lasting for a longer time or the patient's feeling has worsened, for example, can be automatically put off after the treatment room in which the patient has already been brought into an irradiation ready state at that time. With such flexibility, a wasteful waiting time can be reduced and the therapy system can be utilized at maximum efficiency. Hence, treatment can be smoothly conducted on a larger number of patients at higher efficiency. Other advantages reside in that presetting of the irradiation sequence and schedule is not always required, and the schedule can be flexibly changed with ease. This means that the time and labor required for the operator during the treatment can be reduced to a large extent.

A feature of the forth invention resides in comprising a control information forming unit for forming control command information for a first element group disposed in the beam path extended into the selected treatment room, and an information confirming unit for selecting, from among element information including status information representing respective statuses of the first element groups, the status information of the first element group in the beam path extended into the selected treatment room, and confirming that the selected status information is matched with the control command information for the relevant first element group, which is included in the control command information for the first element groups. With this feature, a durable therapy system can be realized which undergoes less reduction of the treatment capability in the event of a trouble. More specifically, even when a trouble occurs in any one of the plurality of treatment rooms and a detected signal having a value other than an ordinary one is outputted from an electromagnet actual operation detecting device associated with the relevant treatment room, selection processing to exclude the relevant treatment room from actual use for the treatment enables the extracting and determining unit to reliably fulfill the intended role, i.e., the comparison between a command value and an actual value, without being affected by the detected signal having such an unordinary value. As a result, even in the case of a trouble occurring in one of the treatment rooms, the treatment operation can be continued by using the remaining normal treatment rooms. It is hence possible to prevent or minimize reduction of the treatment capability and to smoothly continue the treatment. In other words, a durable therapy system can be realized which undergoes less reduction of the treatment capability in the event of a trouble.

A feature of the fifth invention resides in that a plurality of element groups are successively arranged in the beam paths in the direction in which the charged particle beam advances through the beam paths, the element groups including respective elements disposed in the plurality of beam paths, and the element groups are each provided with an alternatively selecting device for alternatively selecting the respective elements in the element groups. With this feature, the beam can be positively prevented from being erroneously introduced to the treatment room in which the irradiation is not scheduled at that time, and safety can be improved. More specifically, in a normal condition, electric power is supplied to only one electromagnet group system to establish one beam transport path so that the beam is introduced to only the treatment room in which the irradiation is to be carried out. On the other hand, if electric power is supplied to the plural electromagnet group systems at the same time because of any error, no beam transport paths are formed and the beam is not introduced to all of the treatment rooms. Thus, it is possible to reliably prevent the beam from being erroneously introduced to the treatment room in which the irradiation is not scheduled at that time, and hence to improve safety.

A feature of the sixth invention resides in operating a first manual input device provided in the treatment room or a control room formed corresponding to the treatment room for inputting a signal indicating an irradiation ready state in the treatment room; thereafter confirming that preparations for transport of the charged particle beam in the beam transport system for introducing the charged particle beam to the irradiation unit in the selected treatment room are completed; displaying ready information regarding the transport of the charged particle beam on a ready state display unit; and then operating a second manual input device provided in the selected treatment room or the corresponding control room for inputting an instruction to start the irradiation.

With that feature, whether to start the irradiation or not can be decided until a point in time immediately before the preparations for transport of the charged particle beam in the relevant beam transport system are completed after the completion of the preparations for irradiation to the patient in the treatment room. As a result, the irradiation can be canceled in a flexible way at any point in time until just before the start of the irradiation, taking into account, for example, that the patient's condition and feeling are in a state sufficiently allowable to receive the irradiation treatment, that the patient's feeling is not worsened, or that the patient does not want to go to the toilet. Hence, the irradiation treatment can be performed on each patient in a safe and prudent manner without problems.

BRIEF DESCRIPTION OF THE DRAWINGS

FIG. 7 is a table showing one example of treatment planning data (patient data) for each patient;

FIG. 8 shows a power supply control table previously stored in a memory provided in a central control system;

FIG. 9 shows another power supply control table, which differs from that shown in FIG. 8, previously stored in the memory provided in the central control system;

FIG. 12 is a table showing a switch changeover pattern stored in a memory provided in a switch yard controller;

FIG. 18 is a time chart showing a flow of operation and control with time in the embodiment; and FIG. 19 is a diagram showing a construction of another example of the switch yard.

DESCRIPTION OF THE PREFERRED EMBODIMENTS

A particle beam therapy system (a particle beam irradiating system) according to one preferable embodiment of the present invention will be described below with reference to the drawings.

Figure 1:
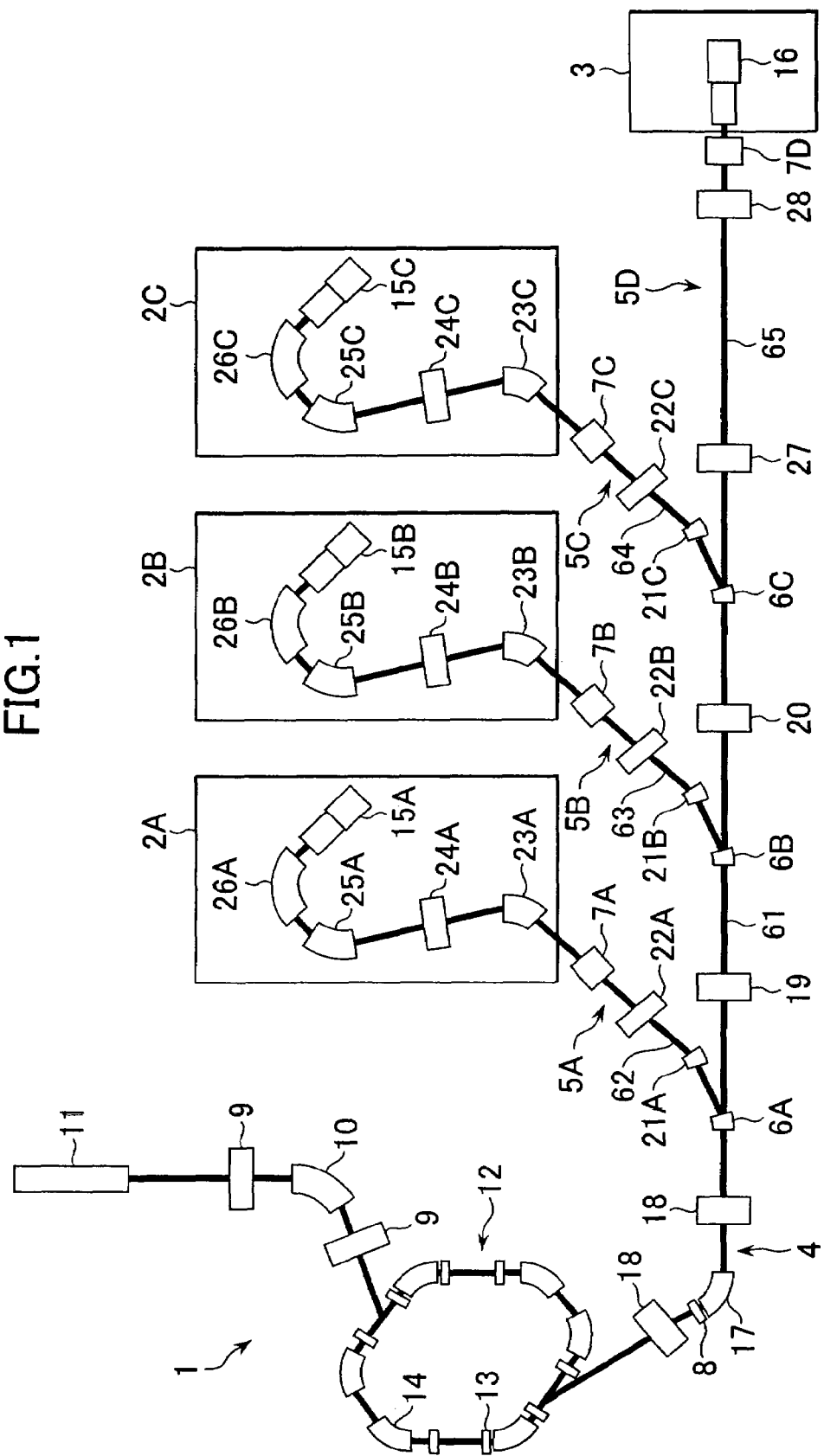
FIG. 1 is a conceptual diagram showing a schematic overall construction of a particle beam therapy system according to one preferable embodiment of the present invention.

A proton beam therapy system constituting a particle beam therapy system of this embodiment comprises, as shown in FIG. 1, a charged particle beam generator 1, four treatment rooms 2A, 2B, 2C and 3, a beam transport system made up of a first beam transport system 4 connected to the downstream side of the charged particle beam generator 1 and a plurality of second beam transport systems 5A, 5B, 5C and 5D branched from the first beam transport system 4, switching electromagnets (path switching devices) 6A, 6B and 6C, shutters (first group of shutters) 7A, 7B, 7C and 7D provided in a one-to-one relation to the treatment rooms, and a shutter (second shutter) 8 common to all the treatment rooms. The first beam transport system 4 serves as a common beam transport system for introducing an ion beam to any of the second beam transport systems 5A, 5B, 5C and 5D.

The charged particle beam generator 1 comprises an ion source (not shown), a pre-stage charged particle beam generator (linac) 11, and a synchrotron 12. Ions (e.g., proton ions (or carbon ions)) generated from the ion source are accelerated by the pre-stage charged particle beam generator (e.g., a linear charged particle beam generator) 11. An ion beam (proton beam) exiting from the pre-stage charged particle beam generator 11 enters the synchrotron 12 through quadrupole electromagnets 9 and a bending electromagnet 10. The ion beam in the form of a charged particle beam (also called a particle beam) is accelerated by being given with energy applied as high-frequency electric power from a high-frequency acceleration cavity (now shown) in the synchrotron 12. After the energy of the ion beam circling in the synchrotron 12 has been increased up to a preset level of energy (e.g., 100 to 200 MeV), a high frequency wave is applied to the ion beam from a high-frequency applying device (not shown) for exiting of the ion beam. With the application of that high frequency wave, the ion beam circling within a stable limit is caused to shift out of the stable limit and to exit (emit) from the synchrotron 12 through an exit deflector (not shown). When causing the ion beam to exit, currents supplied to electromagnets, i.e., quadrupole electromagnets 13 and bending electromagnets 14, disposed in the synchrotron 12 are held at respective setting values and the stable limit is held substantially constant. By stopping the application of the high-frequency electric power to the high-frequency applying device, the exiting (emission) of the ion beam from the synchrotron 12 is stopped.

The ion beam having exited from the synchrotron 12 is transported to the downstream side of the first beam transport system 4. The first beam transport system 4 has a beam path 61 and includes a quadrupole electromagnet 18, a shutter 8, a bending electromagnet 17, another quadrupole electromagnet 18, the switching electromagnet 6A, a quadrupole electromagnet 19, the switching electromagnet 6B, a quadrupole electromagnet 20, and the switching electromagnet 6C, which are disposed in the beam path 61 in this order from the upstream side in the direction of beam advance. The ion beam introduced to the first beam transport system 4 is selectively introduced to one of the second beam transport systems 5A, 5B, 5C and 5D in accordance with the presence or absence of the bending actions produced upon switching between excitation and non-excitation of the above-mentioned electromagnets including the switching electromagnets 6A, 6B and 6C (as described in detail later). The switching electromagnets are each one type of bending electromagnet.

The second beam transport system 5A has a beam path 62 branched from the beam path 61 and connected to an irradiation unit 15A disposed in the treatment room 2A, and it includes a bending electromagnet 21A, a quadrupole electromagnet 22A, a shutter 7A, a bending electromagnet 23A, a quadrupole electromagnet 24A, a bending electromagnet 25A, and a bending electromagnet 26A, which are disposed in the beam path 62 in this order from the upstream side in the direction of beam advance. It can be said that the switching electromagnet 6A is disposed in the beam path 62. The second beam transport system 5B has a beam path 63 branched from the beam path 61 and connected to an irradiation unit 15B disposed in the treatment room 2B, and it includes a bending electromagnet 21B, a quadrupole electromagnet 22B, a shutter 7B, a bending electromagnet 23B, a quadrupole electromagnet 24B, a bending electromagnet 25B, and a bending electromagnet 26B, which are disposed in the beam path 63 in this order from the upstream side in the direction of beam advance. It can be said that the switching electromagnet 6B is disposed in the beam path 63. The second beam transport system 5C has a beam path 64 branched from the beam path 61 and connected to an irradiation unit 15C disposed in the treatment room 2C, and it includes a bending electromagnet 21C, a quadrupole electromagnet 22C, a shutter 7C, a bending electromagnet 23C, a quadrupole electromagnet 24C, a bending electromagnet 25C, and a bending electromagnet 26C, which are disposed in the beam path 64 in this order from the upstream side in the direction of beam advance. Further, the second beam transport system 5D has a beam path 65 extended from the beam path 61 and connected to a fixed irradiation unit 16 disposed in a treatment room 3, and it includes quadrupole electromagnets 27, 28 and a shutter 7D, which are disposed in the beam path 65 in this order from the upstream side in the direction of beam advance. It can be said that the switching electromagnet 6C is disposed in the beam paths 64, 65. The ion beam introduced to the second beam transport system 5A is transported to the irradiation unit 15A through the beam path 62 with excitation of the corresponding electromagnets. The ion beam introduced to the second beam transport system 5B is transported to the irradiation unit 15B through the beam path 63 with excitation of the corresponding electromagnets. The ion beam introduced to the second beam transport system 5C is transported to the irradiation unit 15C through the beam path 64 with excitation of the corresponding electromagnets. Also, the ion beam introduced to the second beam transport system 5D is transported to the irradiation unit 16 through the beam path 65 with excitation of the corresponding electromagnets.

The treatment rooms 2A to 2C include respectively the irradiation units 15A to 15C each mounted to a rotating gantry (not shown) installed in the corresponding treatment room. The treatment rooms 2A to 2C are employed as, e.g., first to third treatment rooms for cancer patients, and the treatment room 3 is employed as a fourth treatment room for ophthalmic treatment, which includes the fixed irradiation unit 16.

Figure 2:
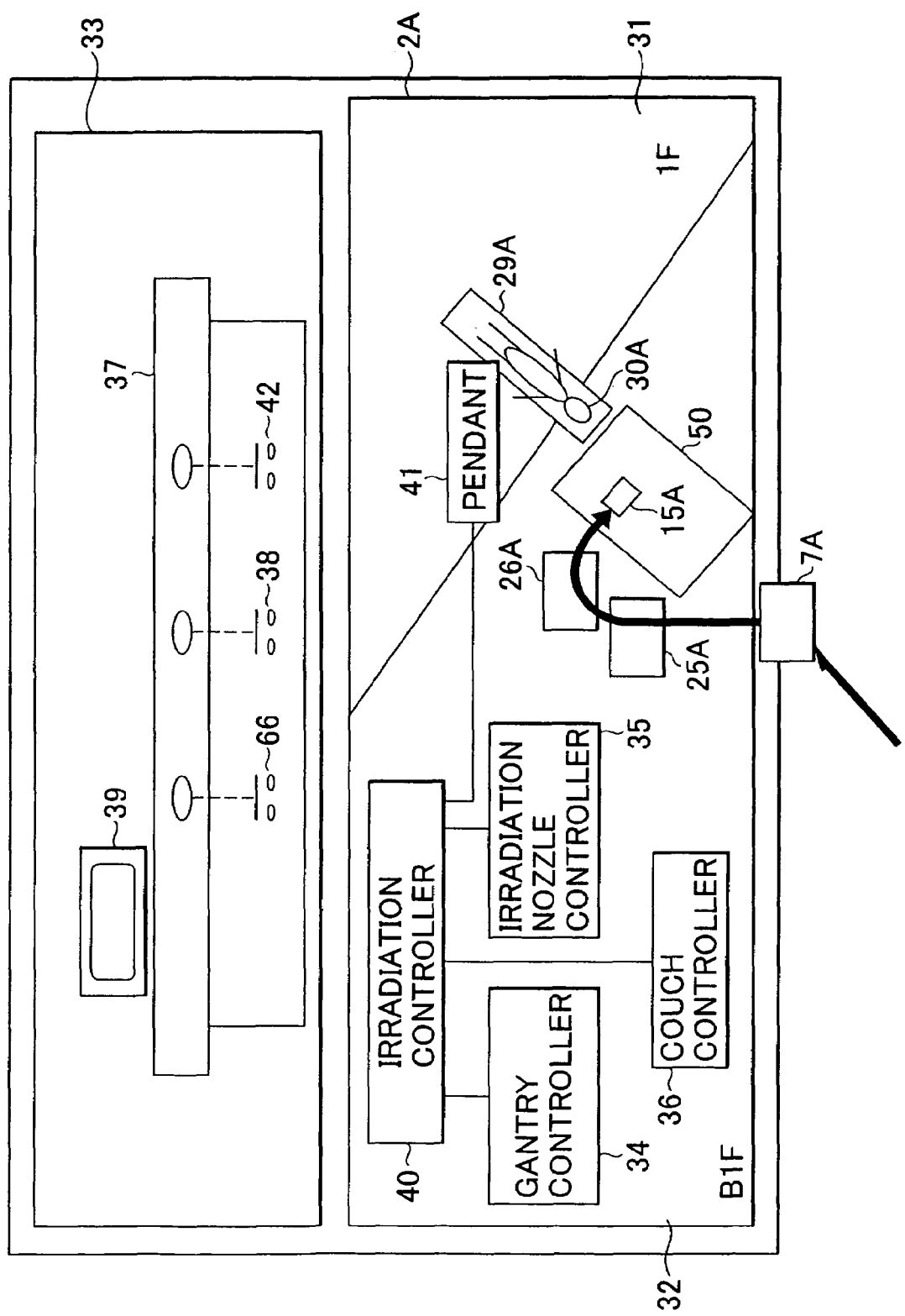
FIG. 2 is a conceptual plan view showing a detailed construction of a treatment room shown in FIG. 1.

The construction and equipment layout in the treatment room 2A will be described below with reference to FIG. 2. Note that since the treatment rooms 2B, 2C also have the same construction and equipment layout as those in the treatment room 2A, a description thereof is omitted here. The treatment room 2A comprises a medical treatment room (zone) 31 formed in the first floor, and a gantry room (zone) 32 formed at a one step lower level, i.e., in the first basement. Further, an irradiation control room 33 is formed outside the treatment room 2A in an adjacent relation to it. The irradiation control room 33 is similarly formed with respect to each of the treatment room 2B and 2C. The irradiation control room 33 is isolated from both the medical treatment room 31 and the gantry room 32. However, the condition of a patient 30A in the medical treatment room 31 can be observed, for example, through a glass window provided in a partition between the irradiation control room 33 and the medical treatment room 31, or by a monitoring image taken by a TV camera (not shown) disposed in the medical treatment room 31.

An inverted U-shaped beam transport subsystem as a part of the second beam transport system 5A and the irradiation unit 15A are mounted to a substantially cylindrical rotating drum 50 of a rotating gantry (not shown). The rotating drum 50 is rotatable by a motor (not shown). A treatment gauge (not shown) is formed inside the rotating drum 50.

Each of the irradiation units 15A to 15C comprises a casing (not shown) connected to the inverted U-shaped beam transport subsystem which is mounted to the rotating drum 50, and a snout (not shown) provided at the fore end of a nozzle through which the ion beam exits. The casing and the snout include, though not shown, a bending electromagnet, a scatterer, a ring collimator, a patient collimator, a bolus, etc. which are arranged therein.

The irradiation field of the ion beam introduced to the irradiation unit 15A in the treatment room 2A from the inverted U-shaped beam transport subsystem through the beam path 62 is roughly collimated by the ring collimator in the irradiation unit 15A and is shaped by the patient collimator in match with the configuration of a tumor in the planar direction perpendicular to the direction of beam advance. Further, the range depth of the ion beam is adjusted by the bolus in match with a maximum depth of the tumor in the body of the patient 30A lying on a patient couch 29A. Prior to the irradiation of the ion beam from the irradiation unit 15A, the patient couch 29A is moved by a couch driver (not shown) to enter the treatment gauge, and is precisely positioned relative to the irradiation unit 15A for the start of the irradiation. The ion beam thus formed by the irradiation unit 15A to have a dose distribution optimum for the particle beam treatment is irradiated to a diseased part (e.g., an area where a tumor or a cancer is produced) of the patient 30A. The energy of the irradiated ion beam is released in the diseased part (hereinafter referred to as a "tumor") to form a high dose region. The movement of the ion beam in each of the irradiation units 15B, 15C and the positioning of the treatment couch are performed in a similar manner to those in the irradiation unit 15A.

In this respect, the rotating drum 50 is rotated by controlling the motor rotation by a gantry controller 34. Also, driving (energization) of the bending electromagnet, the scatterer, the ring collimator, etc. in each of the irradiation units 15A to 15C is controlled by an irradiation nozzle controller 35. Further, driving of the couch driver is controlled by a couch controller 36. These controllers 34, 35 and 36 are all controlled by an irradiation controller 40 disposed in the gantry room 32 inside the treatment room 2A. A pendant 41 is connected to the irradiation controller 40 through a cable extended to the side of the medical treatment room 31, and a doctor (or an operator) standing near the patient 30A transmits a control start signal and a control stop signal to the controllers 34 to 36 through the irradiation controller 40 by manipulating the pendant 41. When the control start signal for the rotating gantry is outputted from the pendant 41, a central control system 100 (described later) takes in rotational angle information of the rotating gantry regarding the patient 30A from treatment plan information stored in a storage 110 and transmits the rotational angle information to the gantry controller 34 through the irradiation controller 40. The gantry controller 34 rotates the rotating gantry based on the rotational angle information.

A treatment (operator) console 37 disposed in the irradiation control room 33 includes a patient ready switch 38 serving as a first manual input device (ready information output device), a display 39 serving as a ready state display unit), an irradiation instruction switch 42 serving as a second manual input device, and an irradiation cancel switch 66 serving as a third manual input device. The functions of those components will be described in more detail later. Still another irradiation control room 33 is separately formed for the treatment room 3.

Figure 3:
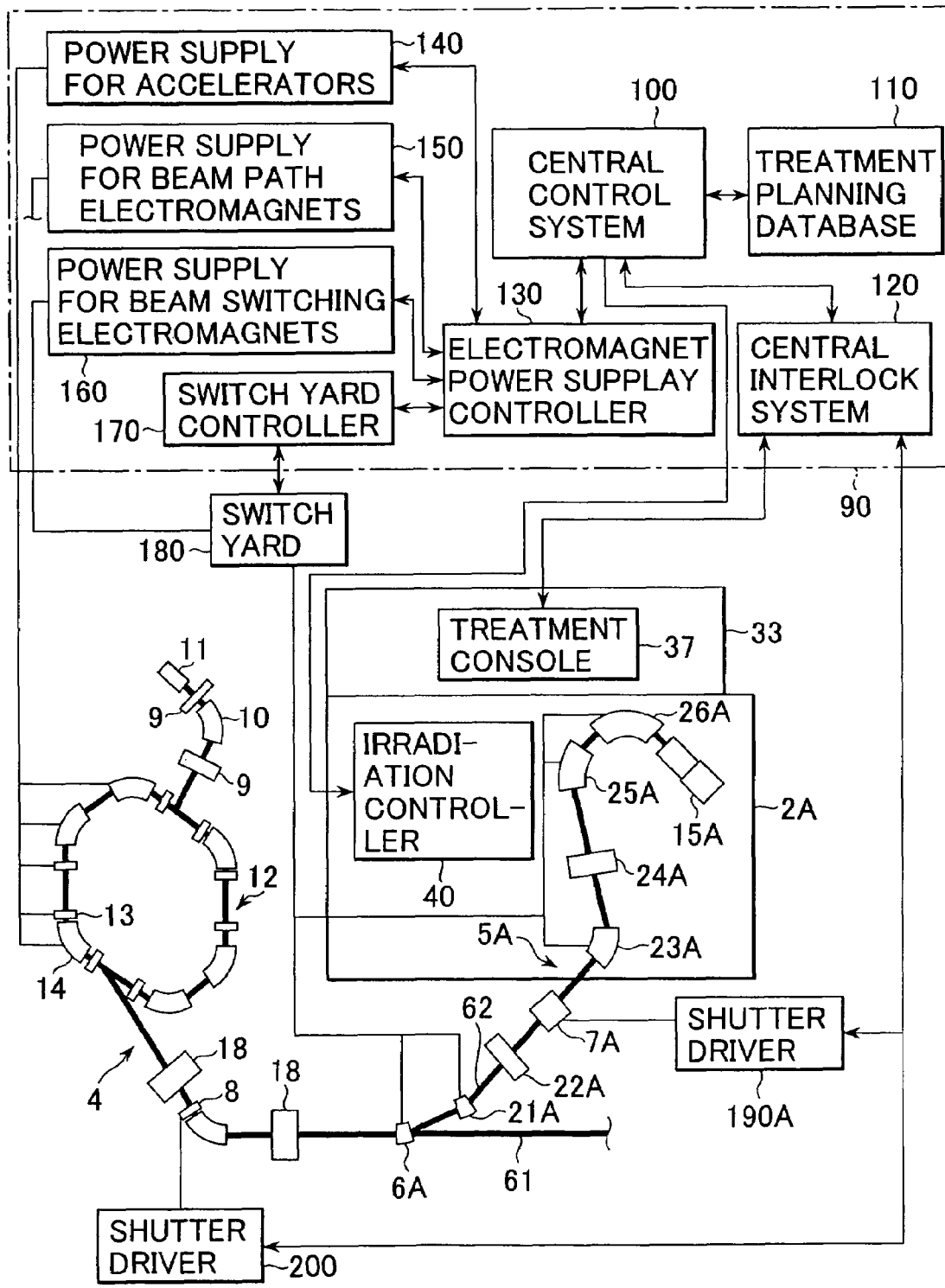
FIG. 3 is a block diagram showing a control system in the particle beam therapy system according to the one embodiment of the present invention.

A control system equipped in the proton beam therapy system of this embodiment will be described below with reference to FIG. 3. A control system 90 comprises a central control system 100, a storage 110 storing a treatment planning database, a central interlock system (safety device) 120, an electromagnet power supply controller 130, a power supply device for the accelerators (hereinafter referred to as an "accelerator power supply") 140, a power supply device for the beam path electromagnets (hereinafter referred to as a "beam path power supply") 150, a power supply device for the beam switching electromagnets (hereinafter referred to as an "switching power supply") 160, and a switch yard controller 170. Further, the proton beam therapy system of this embodiment includes a switch yard 180, shutter drivers 190A to 190D, a shutter driver 200, and a shutter driver 210 (not shown in FIG. 3, see FIG. 15 described later). Note that, although the construction of only one 2A of the treatment rooms 2A to 2C is shown in FIG. 3 for the sake of simplicity of the drawing, the other two treatment rooms 2B, 2C are also similarly constructed.

The patient 30A to be subjected to the irradiation treatment utilizing the ion beam enters one of the treatment rooms 2A to 2C. At that time, the operator (or the doctor, this is similarly applied to the following description) inputs an identifier (e.g., the so-called ID number), namely patient identification information allocated in a one-to-one relation to each patient 30A beforehand, through a patient ID input device (e.g., a PC) 43 provided, for example, on the treatment console 37 in the irradiation control room 33. As an alternative, an identifier (e.g., barcode information) may be written on an attachment wearing on the body of the patient 30A (e.g., a belt or the like fitted on a patient's wrist), and the identifier may be read by a not-shown identifier reader (e.g., a barcode reader) disposed at an inlet of the treatment room when the patient enters the treatment room. Because the patient ID input device 43 is provided for each of the treatment rooms 2A to 2C, the patient identification information is outputted to a CPU (central processing unit) 101 in a central control system 100 together with treatment room information representing the relevant treatment room (e.g., the treatment room number), which the patient 30A has entered, while making those data correspondent to each other.

On the other hand, when the patient 30A having received predetermined examinations, etc. after entering the treatment room lies on the treatment couch 29A and comes into a state ready for the irradiation of the ion beam upon the completion of setups required prior to the irradiation, such as rotation of the rotating gantry and positioning of the treatment couch 29A, the operator goes out of the treatment room 2A, enters the corresponding irradiation control room 33, and depresses the patient ready switch (or button) 38 on the treatment console 37. The patient ready switch 38 may be provided in each of the treatment rooms 2A to 2C if protection of the operator against radiation exposure is reliably ensured by another means. Upon the patient ready switch 38 being depressed, a patient ready signal (irradiation ready signal) is generated and outputted to the central interlock system 120.

Figure 4:
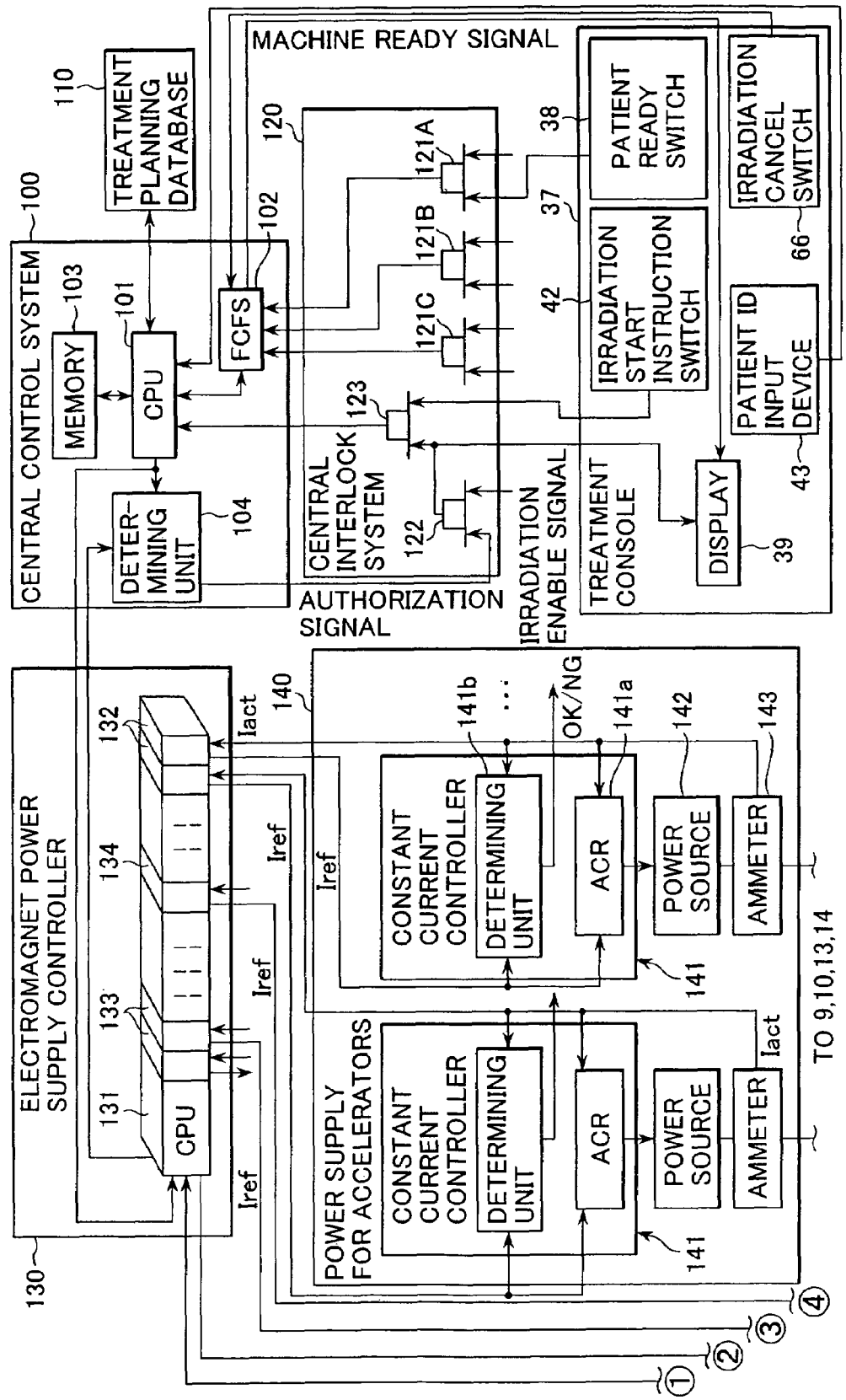
FIG. 4 is a block diagram showing an upper half of more detailed configuration of the control system in the particle beam therapy system according to the one embodiment of the present invention.
Figure 5:
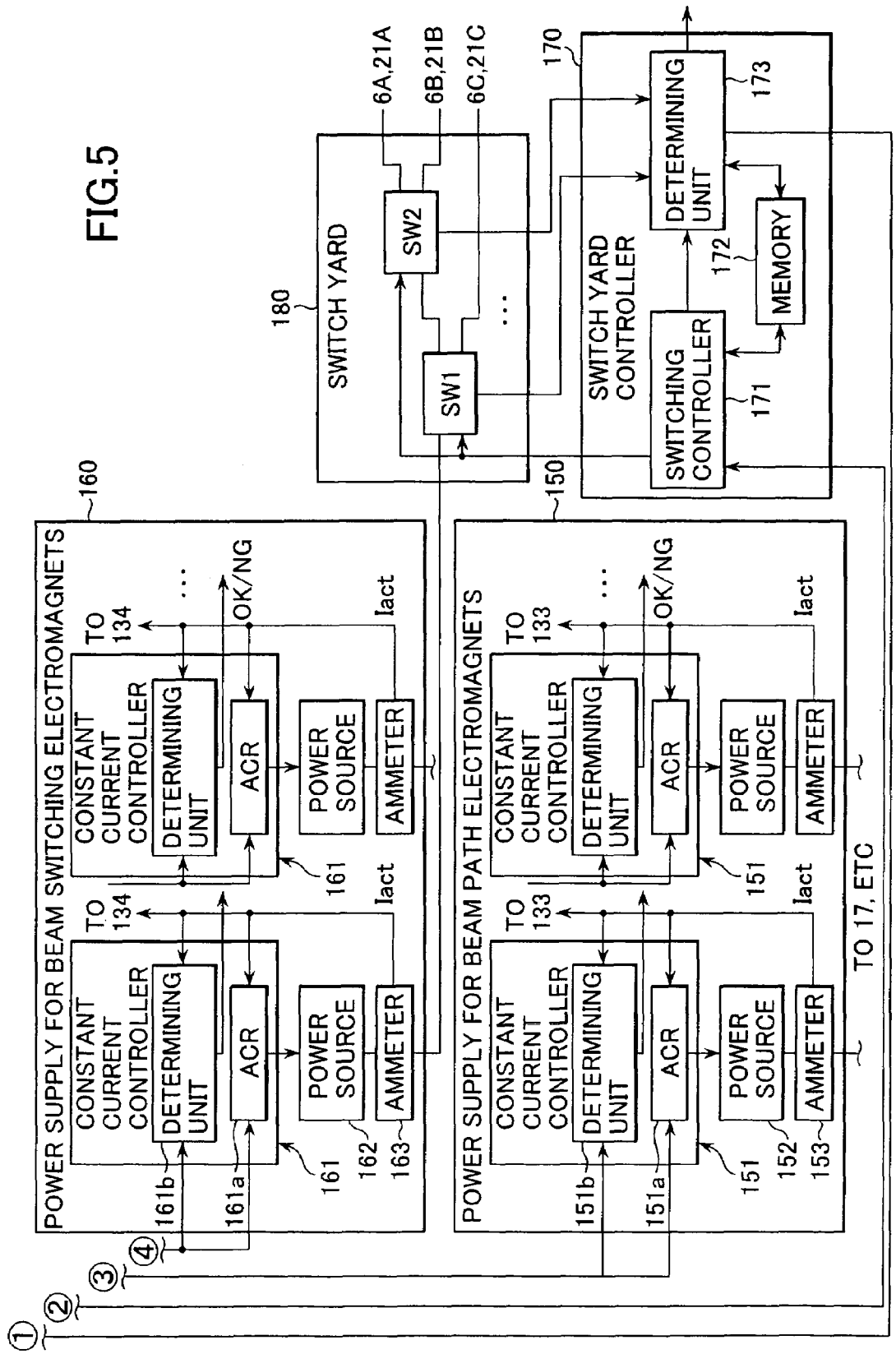
FIG. 5 is a block diagram showing a lower half of more detailed configuration of the control system in the particle beam therapy system according to the one embodiment of the present invention.

The central interlock system 120 comprises (see FIG. 4) three AND circuits 121A, 121B and 121C corresponding respectively to the treatment rooms 2A, 2B and 2C, an AND circuit 121D (not shown, having the same function as the AND circuit 121A) corresponding to the treatment room 2D, and two other AND circuits 122, 123. The AND circuits 121A to 121D receive the patient ready signals outputted from the respective patient ready switches 38 provided in the irradiation control rooms 33 corresponding to the treatment rooms 2A to 2C and 3, and machine ready signals outputted, though not described here in detail, when respective devices and units related to the irradiation of the ion beam in the treatment rooms 2A to 2C and 3 are brought into a standby (ready) state. When the patient ready switch 38 in one of the irradiation control rooms 33 inside the treatment rooms 2A to 2C and 3 is depressed upon the related devices and units being brought into the ready state, an ON signal is inputted from corresponding one of the AND circuits 121A, 121B, 121C and 121D to a first-come, first-served basis controller (First Come First Serve (FCFS)) 102 in the central control system 100.

Figure 6:
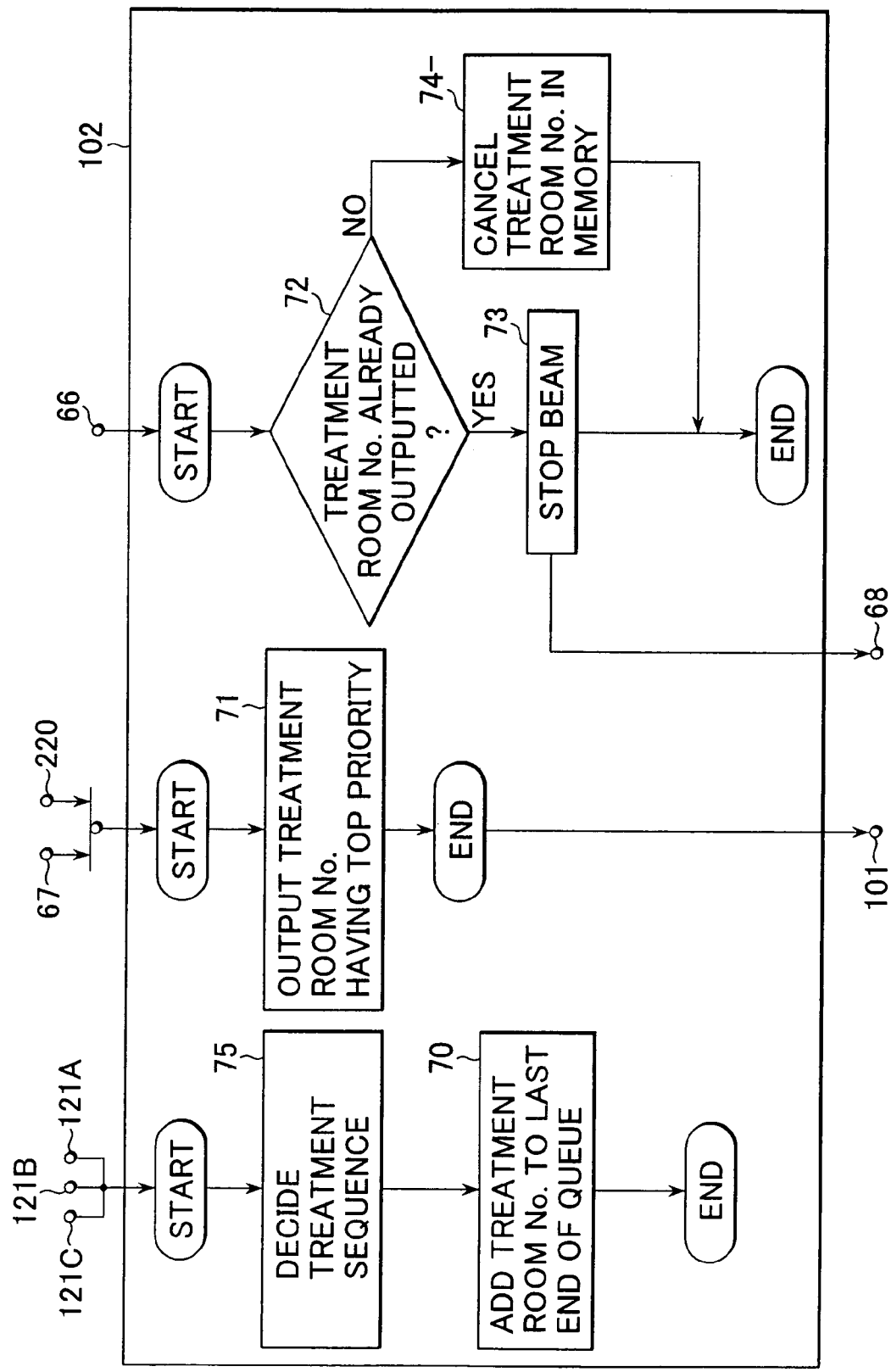
FIG. 6 is a flowchart showing a sequence of control steps executed by a first-come, first-served basis controller.

The processing sequence executed by the First Come First Serve 102 will be described below with reference to FIG. 6. The First Come First Serve 102 has three functions. First one is the function as a treatment sequence deciding device for executing processing of steps 75, 70 in FIG. 6, and second one is the function as a treatment room information outputting device for executing processing of step 71 in FIG. 6. The last third one is the function as a beam irradiation canceling device for executing processing of steps 72 to 74 in FIG. 6. The first function will first be described. Step 75 is a step of deciding the treatment sequence, and step 70 is a step of adding the treatment room number (treatment room information). In the treatment sequence deciding step (step 75), the treatment sequence for the treatment rooms is decided based on the ON signals from the AND circuit 121A corresponding to the treatment room 2A (treatment room No. 1), the AND circuit 121B corresponding to the treatment room 2B (treatment room No. 2), the AND circuit 121C corresponding to the treatment room 2C (treatment room No. 3), and the AND circuit 121D corresponding to the treatment room 3 (treatment room No. 4) such that the ON signals are processed in the sequence in which they have been inputted (i.e., in the order in which the irradiation ready signals have been generated or outputted), namely that the earlier incoming ON signals are processed with higher priority ascending toward the first incoming one. In the treatment room number adding step (step 70), the treatment room number (treatment room information) corresponding to the AND circuit, which has outputted the ON signal having been inputted in accordance with the decided treatment sequence, is added to the last end of an irradiation queue stored in a memory (not shown) of the First Come First Serve 102. With the provision of the AND circuits 121A, 121B, 121C and 121D, even if the operator depresses the patient ready switch 38 by mistake, the ON signal is not outputted because the machine ready signal is not inputted to the relevant AND circuit. It is therefore possible to prevent the operation (e.g., excitation of the electromagnets described later) that may form an undesired beam path.

Next, the second function will be described. In the treatment performed first (e.g., the first treatment in a day), the treatment room number having the top priority in the queue stored in the memory of the First Come First Serve 102 is outputted (step 71). The treatment room number (No. 1, No. 2, No. 3 or No. 4) having the top priority is inputted to the CPU 101 (see FIG. 4) in the central control system 100. For the treatment room numbers having the second and subsequent priority, when an irradiation completion signal (described later) outputted from a dose detection controller 220 (see FIG. 15) or a beam stop signal (described later) outputted from an OR circuit 69 (see FIG. 17) in the central interlock system 120 is inputted through a terminal 67, the treatment room number having the top priority at that time is outputted from the First Come First Serve 102 to the CPU 101. Each of the irradiation completion signal and the beam stop signal serves as an irradiation end signal, and the treatment room number having the top priority is outputted in response to the irradiation end signal. Each time the treatment room number having the top priority is outputted, the treatment room numbers in the irradiation queue stored in the above-mentioned memory are each forwarded by one in the output sequence.

Finally, the third function will be described. This function is actuated when the irradiation of the ion beam to the patient 30A should be stopped in the case that the condition of the patient 30A lying on the treatment couch 29A has worsened during a period until the irradiation instruction switch 42 is depressed after depression of the patient ready switch 38 corresponding to one treatment room. For example, if the condition of the patient 30A in the No. 1 treatment room 2A has worsened, the doctor depresses the irradiation cancel switch 66 in the irradiation control room 33 corresponding to the treatment room 2A. A resulting irradiation cancel signal is inputted to the First Come First Serve 102, followed by determining in step 72 whether the relevant treatment room number has already been outputted. If the determination result is "NO", the relevant treatment room number (No. 1 in this case) in the memory of the First Come First Serve 102 is canceled (step 74). At this time, the treatment room numbers put in the irradiation queue subsequent to the canceled treatment room number are each forwarded by one. If the determination result in step 72 is "YES", a beam stop signal is outputted to the charged particle beam generator 1 to cancel the treatment room number having already been outputted (step 73). The beam stop signal is outputted from the OR circuit 69 (see FIG. 17) in the central interlock system 120 through a terminal 68, whereby the operation of the charged particle beam generator 1 is forcibly stopped. With the third function, it is possible to stop the irradiation of the ion beam toward the patient lying on the treatment couch 29A, whose condition has worsened.

The First Come First Serve 102 outputs a plurality of treatment room numbers, which are stored in the internal memory in the treatment sequence, to the displays 39 disposed on the treatment consoles 37 in the irradiation control rooms 33 corresponding to the treatment rooms 2A to 2C and 3 in the same sequence. Because the treatment room numbers are displayed on each display 39 in the treatment sequence, the operator present in each of the irradiation control rooms 33 corresponding to the treatment rooms 2A to 2C and 3 is able to know the treatment sequence allocated to the relevant treatment room at that time. In addition to the display mentioned above, the First Come First Serve 102 may further display, on each display 39, how many patients are now waiting prior to the relevant patient, approximately how long time the relevant patient must wait until the start of the treatment, or the like. As an alternative, instead of displaying such detailed information, it is also possible to only the fact that the priority order is not the first (i.e., the irradiation cannot be started at once and the relevant patient must wait for a time required for the treatment of at least one other patient).

The treatment room number having the top priority (i.e., the treatment room number selected to start the irradiation therein at that time) outputted from the First Come First Serve 102 in step 71, namely the treatment room number of the selected treatment room, is inputted to the CPU 101 in the central control system 100. For convenience of the following description, that treatment room number is assumed here to be "No. 1". In other words, the treatment room 2A is assumed to be the selected treatment room.

Based on that treatment room number and the above-described patient identification information inputted from the patient ID input device 43 in each of the treatment rooms 2A to 2C and 3 in correspondence to the treatment room information, the CPU 101 recognizes the patient who is going to receive the ion beam irradiation treatment from that time and the treatment room to which the ion beam is to be introduced for the treatment. Then, the CPU 101 accesses the treatment planning database stored in the storage 110. The treatment planning database records and accumulates therein treatment planning data that has been prepared by doctors in advance for all the patients who will receive the irradiation treatment.

One example of the treatment planning data (patient data) stored in the storage 110 for each patient will be described with reference to FIG. 7. The treatment planning data contains the patient ID number, dose (per one shot), irradiation energy, irradiation direction (not shown), irradiation position (not shown), etc. Because the patient identification information and the treatment room information are made correspondent to each other as described above, the treatment planning data is not always required to contain the treatment room information. It is needless to say that the treatment planning data may include the treatment room information for convenience in carrying out the treatment.

By employing the inputted patient identification information, the CPU 101 reads from the storage 110 the treatment planning data for the patient who is going to receive the ion beam irradiation treatment from that time. Among the treatment planning data per patient, important one is a value of the irradiation energy. A control pattern for excitation power supplied to each electromagnet mentioned above is decided depending on the value of the irradiation energy.

The power supply control table previously stored in a memory 103 provided in the central control system 100 will be described with reference to FIG. 8. As shown in FIG. 8, corresponding to respective values (70, 80, 90, . . . [MeV] in an illustrated example) of the irradiation energy, various parameters are preset which include excitation power values (though simply denoted by " . . . " in the table, concrete numerical values are put in fact) or patterns of the excitation power values supplied to the quadrupole electromagnets 9, 13 and the bending electromagnets 10, 14 in the charged particle beam generator 1 including the synchrotron 12, the quadrupole electromagnets 18, 19, 20 and the bending electromagnet 17 in the first beam transport system 4, the quadrupole electromagnets 22A, 24A in the second beam transport system 5A for the treatment room 2A, the quadrupole electromagnets 22B, 24B in the second beam transport system 5B for the treatment room 2B, the quadrupole electromagnets 22C, 24C in the second beam transport system 5C for the treatment room 2C, and the quadrupole electromagnet 28 in the second beam transport system 5D for the treatment room 3, as well as electromotive values (though simply denoted by " . . . " in the table; concrete numerical values are put in fact) of switching power sources 162-1, 162-2, 162-3 and 162-4 (described later).

In this embodiment, the various electromagnets and power supplies are controlled by using the treatment planning data per patient, shown in FIG. 8, to control switching of the beam path. One major feature of this embodiment resides in that, when the beam path is switched over such that the ion beam is introduced from the beam path 61 to one of the four beam paths 62, 63, 64 and 65 for guiding the ion beam to the four treatment rooms 2A, 2B, 2C and 3, respectively, the electromagnets not directly taking part in setting of switching of the relevant beam path are not positively controlled and their states are not taken into consideration. This point will be described below with reference to FIG. 9.

A power supply control table shown in FIG. 9 is previously stored in the memory 103 provided in the central control system 100. This control table represents control of power supply different from that represented in the power supply control table shown in FIG. 8. As shown in FIG. 9, it is preset that the quadrupole electromagnets 9, 13 and the bending electromagnets 10, 14 in the charged particle beam generator 1 including the synchrotron 12, the quadrupole electromagnets 18, 19, 20 and the bending electromagnet 17 in the first beam transport system 4, the quadrupole electromagnets 22A, 24A in the second beam transport system 5A for the treatment room 2A, the quadrupole electromagnets 22B, 24B in the second beam transport system 5B for the treatment room 2B, the quadrupole electromagnets 22C, 24C in the second beam transport system 5C for the treatment room 2C, and the quadrupole electromagnet 28 in the second beam transport system 5D for the treatment room 3 are controlled (indicated by "ON" in the table) corresponding to the treatment room numbers (No. 1 to No. 4). A box denoted by "No Care" in the table represents that control data for the relevant unit (e.g., the quadrupole electromagnet 22B) is not included. This is similarly applied to other tables described later. For example, when the ion beam is to be transported to the treatment room 2A through the second beam transport system 5A, the quadrupole electromagnets 9, 13 and the bending electromagnets 10, 14 in the charged particle beam generator 1, the quadrupole electromagnet 18 and the bending electromagnet 17 in the first beam transport system 4, and the quadrupole electromagnets 22A, 24A in the second beam transport system 5A must be ON-controlled because they are positioned on the beam path through which the ion beam is introduced to the treatment room 2A. On the other hand, the other electromagnets positioned on the other beam paths than the relevant one impose essentially no influences upon control for changing over the beam path regardless of whether the other electromagnets are turned ON or OFF. Incidentally, when information is added to the box of "No Care", the added information is selected to be free from the relevant unit such that control for the relevant unit is not executed.

Similarly, when the ion beam is to be transported to the treatment room 2B through the second beam transport system 5B, the quadrupole electromagnets 20, 27 in the first beam transport system 4, the quadrupole electromagnets 22A, 24A in the second beam transport system 5A for the treatment room 2A, the quadrupole electromagnets 22C, 24C in the second beam transport system 5C for the treatment room 2C, and the quadrupole electromagnet 28 in the second beam transport system 5D for the treatment room 3 are not controlled. Also, when the ion beam is to be transported to the treatment room 2C through the second beam transport system 5C, the electromagnets 22A, 24A, 22B, 24B, 27 and 28 are not controlled. Further, when the ion beam is to be transported to the treatment room 3 through the second beam transport system 5D, the electromagnets 22A, 24A, 22B, 24B, 22C and 24C are not controlled.

The CPU 101 functions as a control information forming unit and, by using the treatment planning data shown in FIG. 7 and the power supply control table shown in FIGS. 7 and 8, it forms control command data (control command information) for controlling the electromagnets, which are disposed in the charged particle beam generator 1 and the various beam paths, depending on the patient who is going to receive the irradiation from that time.

Figure 10:
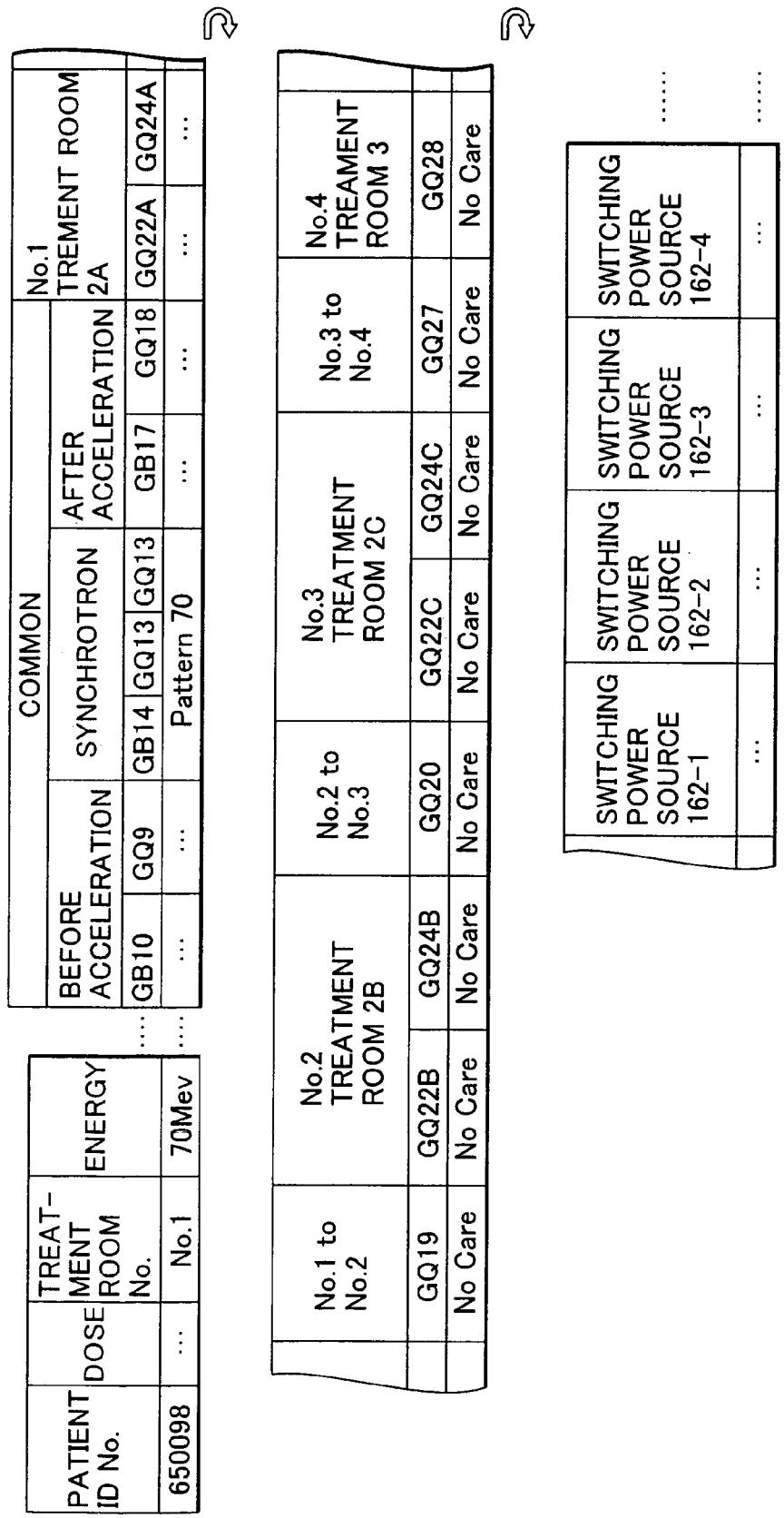
FIG. 10 shows one example of control command data.

One example of the control command data thus prepared by the CPU 101 will be described with reference to FIG. 10. In this example, the patient is subjected to the irradiation at energy of 70 MeV in the treatment room 2A (i.e., the treatment room No. 1). The control command data in this example is formed by combining, subsequent to the patient data shown in FIG. 7, data resulting from extracting those of the numerical values and the pattern in the boxes corresponding to "70 MeV" shown in FIG. 8, which are denoted by "ON" in FIG. 9 (note that all the electromagnets are assigned with addresses for communication of the respective control data). At least at this time, as shown in FIG. 10, the treatment room number must be included in the control command data for later-described control for changing over the beam path. From this point of view, the control command data always corresponds to any number (one of No. 1 to No. 4) of the treatment rooms 2A to 2C and 3 (hence it is control command data per treatment room). Thus, the CPU 101 can also be said as functioning as a unit for forming control information per treatment room.

The CPU 101 outputs the thus-formed control command data to the electromagnet power supply controller 130 and a determining unit (information confirming unit) 104 which is separately provided in the central control system 100.

The electromagnet power supply controller 130 comprises a CPU (central processing unit) 131 having the processing function, and input/output conversion (e.g., so-called A/D, A/I, D/O and D/I) controllers having input/output units in the same number as the total number of constant current controllers and determining units in the accelerator power supply 140, the beam path power supply 150, and the switching power supply 160, to and from which signals are transmitted and received. The input/output conversion controllers comprises an input/output conversion controller 132 for transferring a signal with respect to the accelerator power supply 140, an input/output conversion controller 133 for transferring a signal with respect to the beam path power supply 150, and an input/output conversion controller 134 for transferring a signal with respect to the switching power supply 160.

The CPU 131 in the electromagnet power supply controller 130 decomposes the control command data inputted from the CPU 101 in the central control system 100 again into components (element control information) required for control of the accelerator power supply 140, the beam path power supply 150, and the switching power supply 160, followed by distributing the respective data components to the corresponding input/output conversion controllers 132, 133 and 134.

In other words, the CPU 131 distributes a part of the control command data shown, by way of example, in FIG. 10, i.e., power supply control data (element control information), which is related to the quadrupole electromagnets 9, 13 and the bending electromagnets 10, 14 in the charged particle beam generator 1, to the input/output conversion controller 132 corresponding to the accelerator power supply 140.

Generally, the CPU 131 distributes, to the input/output conversion controller 133 corresponding to the beam path power supply 150, a part of the control command data shown, by way of example, in FIG. 10 other than those related to the charged particle beam generator 1, i.e., power supply control data (element control information) related to the quadrupole electromagnets 18, 19, 20 and the bending electromagnet 17 in the first beam transport system 4, the quadrupole electromagnets 22A, 24A in the second beam transport system 5A for the No. 1 treatment room 2A, the quadrupole electromagnets 22B, 24B in the second beam transport system 5B for the No. 2 treatment room 2B, the quadrupole electromagnets 22C, 24C in the second beam transport system 5C for the No. 3 treatment room 2C, and the quadrupole electromagnet 28 in the second beam transport system 5D for the No. 4 treatment room 3. That power supply control data is distributed in a different way depending on the treatment room information contained in the control command data, i.e., the information of the treatment room. For example, when the treatment room number contained in the control command data is "No. 1" as described above, the CPU 131 distributes, to the input/output conversion controller 133, the power supply control data for the quadrupole electromagnets 18, 22A and 24A and the bending electromagnet 17 which are arranged in the beam paths for introducing the ion beam from the synchrotron 12 to the treatment room designated by the treatment room number (i.e., the selected treatment room). When the control command data contains information of another treatment room number, the CPU 131 distributes the power supply control data for the relevant electromagnets in a similar manner.

Furthermore, the CPU 131 distributes treatment room data (No. 1 in the example of FIG. 10) in the control command data shown, by way of example, in FIG. 10 to the input/output conversion controller 134 corresponding to the switching power supply 160.

The accelerator power supply 140 comprises constant current controllers 141, power sources 142, and ammeters 143 in a multiple number of units each constituted by these three components (e.g., in the same number as that of current output targets, namely that of the quadrupole electromagnets 9, 13 and the bending electromagnets 10, 14 as control targets). Each of the constant current controllers 141 comprises a control unit (so-called ACR) 141a having the function of control to hold a constant current at a desired value, and a determining unit (element information confirming unit) 141b.

The power supply control data (including a current value command signal) for each of the quadrupole electromagnets 9, 13 and the bending electromagnets 10, 14, which is outputted from the input/output conversion controller 132, is inputted to the ACR 141a of the constant current controller 141 provided corresponding to each of the electromagnets. The ACR 141a outputs a current value command signal to the power source 142 based on the inputted control data so that the power source 142 is turned on and controlled in accordance with the current value command signal. As a result, the magnitude of the current supplied from the power source 142 to the relevant electromagnet, e.g., the bending electromagnet 10, is controlled. A value of the current outputted from the power source 142 is detected by the ammeter 143, and a detected actual current value $I_{act}$ is inputted to the ACR 141a and the determining unit 141b. The ACR 141a performs feedback control based on the actual current value $I_{act}$ outputted from the ammeter 143. With the feedback control, the current having a value (i.e., a current value varying with time depending on the beam acceleration and exiting status as known) substantially equal to that of the power supply control data is supplied to the bending electromagnet 10 as the control target. The current value command signal (current command value or current reference $I_{ref}$) from the ACR 141a is also inputted to the determining unit 141b. The determining unit 141b compares the current command value (element control information) $I_{ref}$ and the actual current value (actual current data or element status information) $I_{act}$ to determine whether the actual current value $I_{act}$ is matched with the current command value $I_{ref}$ in consideration of an allowable margin as well. Stated another way, the determination as to the match between the actual current value and the current command value means confirmation that the actual current value is substantially equal to the current command value. The other constant current controllers 141 also function in a similar manner such that currents having respective current command values $I_{ref}$ are supplied to the quadrupole electromagnets 9, 13 and the other bending electromagnet 14. Accordingly, all the electromagnets are excited by the constant currents having the respective current command values $I_{ref}$, and hence the beam acceleration adapted for the treatment condition for the patient who is going to receive the irradiation can be achieved with the synchrotron 12.

In this respect, for the purpose of confirming the operation of the overall system described later, the ACR 141a outputs a signal representing the actual current value (element status information) from the ammeter 143 to the input/output conversion controller 132. The determining unit 141b outputs a result of the above-described determination (also called determination information or confirmation information), i.e., "OK" (or "NG"), to the CPU 131 in the electromagnet power supply controller 130 (as described later). If the determination result indicates the occurrence of an error (abnormality), the determining unit 141b diagnoses the presence or absence of an error in the corresponding power source 142 and ACR 141a, and then outputs a diagnosis result ("OK" (or "NG") for each diagnosis target) to the central interlock system 120. The other determining units 141b also function in a similar manner, thereby outputting the determination results and the diagnosis results to the central interlock system 120.

As in the accelerator power supply 140, the beam path power supply 150 comprises constant current controllers 151, power sources 152, and ammeters 153 in a multiple number of units each constituted by these three components (e.g., in the same number as that of current output targets, namely that of the quadrupole electromagnets 18, 19, 20, 22A-22C, 24A-24C, 27 and 28 and the bending electromagnet 17 as control targets). Each of the constant current controllers 151 comprises a control unit (ACR) 151a having the function of control to hold a constant current at a desired value, and a determining unit (element information confirming unit) 151b.

The power supply control data for each corresponding electromagnet, which is outputted from the input/output conversion controller 133, is inputted to the ACR 151a of the constant current controller 151 provided corresponding to each of the electromagnets (e.g., the electromagnets disposed in the beam path through which the ion beam introduced to the selected treatment room 2A passes). Similarly to the constant current controller 141 of the accelerator power supply 140, based on the inputted control data, the ACR 151a of one constant current controller 151 turns on the corresponding power source 152 and controls it through feedback of an actual current value detected by the ammeter 153. As a result, a current outputted from the power source 152 is adjusted to have a current command value $I_{ref}$. Thus, a constant current having the current command value $I_{ref}$ is supplied from the power source 152 to corresponding one of the quadrupole electromagnets 18, 22A, 24A and the bending electromagnet 17 through which the ion beam introduced to the selected treatment room 2A passes. The electromagnet is thereby excited. Further, the ACR 151a outputs information of the actual current value $I_{act}$ to the input/output conversion controller 133.

Similarly to the determining unit 141b, the determining unit 151b of the constant current controller 151 compares the actual current value $I_{act}$ detected by the ammeter 153 with the current command value $I_{ref}$ to determine a match between them (i.e., to confirm whether the actual current value $I_{act}$ is substantially equal to the current command value $I_{ref}$). Then, the determining unit 151b outputs a determination result (also called determination information or confirmation information), i.e., "OK" (or "NG"), and a diagnosis result ("OK" (or "NG") for each diagnosis target) to the central interlock system 120. The ACR's 151a and the determining units 151b of the other constant current controllers 151 also operate with similar functions to those described above.

As in the accelerator power supply 140, the switching power supply 160 comprises constant current controllers 161, power sources 162, and ammeters 163 in a multiple number of units each constituted by these three components (e.g., four units because there are four power sources 162). Each of the constant current controllers 161 comprises a control unit (ACR) 161a having the function of control to hold a constant current at a desired value, and a determining unit 161b.

Figure 11:
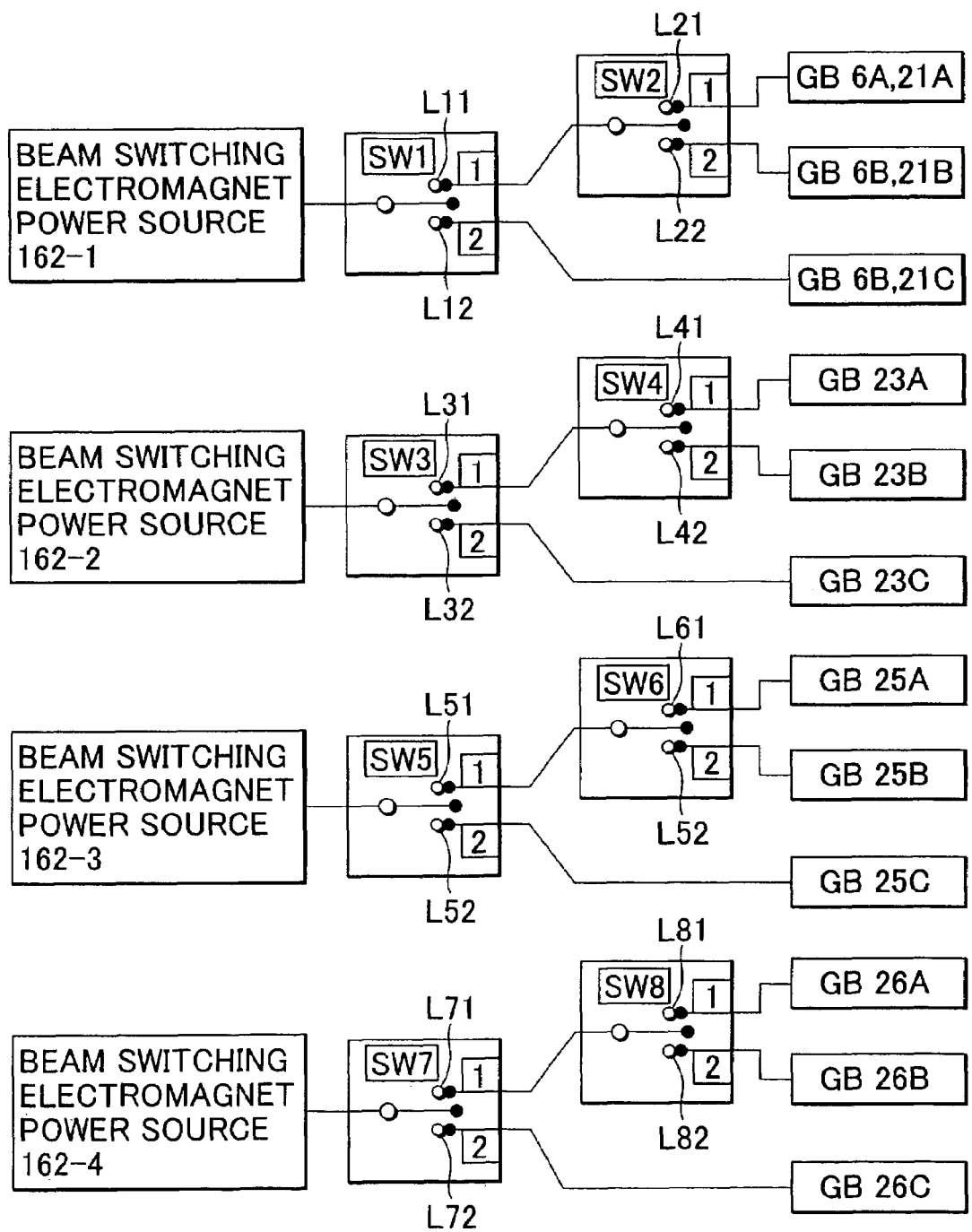
FIG. 11 is a diagram showing a detailed construction of a switch yard.

The power supply control data for each switching power source 162 (corresponding one of switching power sources 162-1, 162-2, 162-3 and 162-4 shown in FIG. 11), which is outputted from the input/output conversion controller 134, is inputted to the ACR 161a of the constant current controller 161 provided corresponding to each switching power source 162. Based on the inputted control data, the ACR 161a of one constant current controller 161 turns on the corresponding switching power source 162 and controls it through feedback of an actual current value detected by the ammeter 163. As a result, a constant current having a current command value $I_{ref}$, outputted from the switching power source 162, is supplied to a relevant one of changeover switch groups (see FIG. 11), i.e., a power supply target, provided in the switch yard 180. Current supply to the corresponding electromagnet under control of the changeover switch groups will be described later. In addition, the ACR 161a outputs information of the actual current value $I_{act}$ detected by the ammeter 163 to the input/output conversion controller 134.

Similarly to the determining unit 141b, the determining unit 161b of the constant current controller 161 determines a match between the actual current value $I_{act}$ detected by the ammeter 163 and the current command value $I_{ref}$ (i.e., confirms whether the actual current value $I_{act}$ is substantially equal to the current command value $I_{ref}$). Then, the determining unit 161b outputs a determination result (also called determination information or confirmation information), i.e., "OK" (or "NG"), and a diagnosis result ("OK" (or "NG") for each diagnosis target) to the central interlock system 120. The ACR's 161a and the determining units 161b of the other constant current controllers 161 also operate with similar functions to those described above.

The CPU 131 in the electromagnet power supply controller 130 outputs the treatment room number data (No. 1 in the example shown in FIG. 10) to the switch yard controller 170 as well. The switch yard controller 170 comprises a switching controller 171, a memory 172, and a determining unit 173. The switching controller 171 carries out changeover control of various switches provided in the switch yard 180 in accordance with the treatment room number data from the CPU 131.

The detailed construction of the switch yard 180 will be described below with reference to FIG. 11. The switch yard 180 comprises four switch groups. A first switch group has switches SW1, SW2, a second switch group has switches SW3, SW4, a third switch group has switches SW5, SW6, and a fourth switch group has switches SW7, SW8. By changing over the switches of those switch groups, the bending electromagnets 6A-6C, 21A-21C, 23A-23C, 25A-25C, and 26A-26C in the second beam transport systems 5A, 5B and 5C are selectively controlled. Each of the switches contains a mechanical switching device (including the so-called double throw mechanical switch) that serves as an alternative selector with an alternative switching function.

In the first switch group, an input terminal of the switch SW1 is connected to one switching power source 160 of the switching power supply 162, and one input terminal of the switch SW2 is connected to an output terminal 1 of the switch SW1. The switching electromagnet (bending electromagnet) 6A and the bending electromagnet 21A arranged electrically in series are connected to one output terminal 1 of the switch SW2. The switching electromagnet (bending electromagnet) 6B and the bending electromagnet 21B arranged electrically in series are connected to the other output terminal 2 of the switch SW2. The switching electromagnet (bending electromagnet) 6C and the bending electromagnet 21C arranged electrically in series are connected to the other output terminal 2 of the switch SW1. With the later-described switch changeover operation by the switch yard controller 170, a current is supplied from the switching power source 162-1 to the switching electromagnet 6A for bending the ion beam from the beam path 61 to the beam path 62 that is extended to the irradiation unit 15A in the selected treatment room 2A. The switching electromagnet 6A is thereby excited. At this time, the switch SW1 makes a contact with the output terminal 1 thereof and the switch SW2 makes a contact with the output terminal 1 thereof.

Terminals of the switches SW3, SW4 of the second switch group are connected to each other similarly to those of the switches of the first switch group, and the switching power source 162-2 is connected to an input terminal of the switch SW3. The bending electromagnet 23A is connected to one output terminal 1 of the switch SW4, the bending electromagnet 23B is connected to the other output terminal 2 of the switch SW4, and the bending electromagnet 23C is connected to the other output terminal 2 of the switch SW3.

Also, terminals of the switches SW5, SW6 of the third switch group are connected to each other similarly to those of the switches of the first switch group, and the switching power source 162-3 is connected to an input terminal of the switch SW5. The bending electromagnet 25A is connected to one output terminal 1 of the switch SW6, the bending electromagnet 25B is connected to the other output terminal 2 of the switch SW6, and the bending electromagnet 25C is connected to the other output terminal 2 of the switch SW5.

Further, terminals of the switches SW7, SW8 of the fourth switch group are connected to each other similarly to those of the switches of the first switch group, and the switching power source 162-4 is connected to an input terminal of the switch SW7. The bending electromagnet 26A is connected to one output terminal 1 of the switch SW8, the bending electromagnet 26B is connected to the other output terminal 2 of the switch SW8, and the bending electromagnet 26C is connected to the other output terminal 2 of the switch SW7.

With the operations of the switch groups, respective currents are supplied to the bending electromagnets 23A, 25A and 26A arranged in the beam path 62 to excite them so that the ion beam is introduced to the selected treatment room 2A.

The above-described construction of the switch yard 180 is further intended to constitute a first electromagnet group corresponding to the first switch group, a second electromagnet group corresponding to the second switch group, a third electromagnet group corresponding to the third switch group, and a fourth electromagnet group corresponding to the fourth switch group. These electromagnet groups are arranged respectively in the beam paths 62, 63 and 64 in order in the direction of advance of the ion beam. Looking at the electromagnet groups more closely, one of the electromagnets in each electromagnet group is disposed in each of the beam paths 62, 63 and 64. The electromagnets included in one electromagnet group are all connected to a common power source and are supplied with currents through alternative changeover of the switches. In each electromagnet group, an electric power is supplied to only one electromagnet from the power source, and no power is supplied to the remaining electromagnets from the same power source.

Stated another way, the first, second, third and fourth switch groups constitute three different electromagnet groups arranged respectively in the beam routs 62, 63 and 64 for introducing the ion beam to the treatment rooms 2A, 2B and 2C. Thus, with the operations of the switches in the switch groups, five electromagnets included in one electromagnet group arranged along the relevant beam path (beam path 62) extended to the selected treatment room (e.g., the treatment room 2A) are excited by the four switching power sources 162-1, 162-2, 162-3 and 162-4.

The changeover operation of each switch in the switch yard 180 is performed under control of the switch yard controller 170. The switch yard controller 170 comprises the switching controller 171, the memory 172, and the determining unit 173. The memory 173 stores information of reference changeover patterns, shown in FIG. 12, for the switches SW1 to SW8. In accordance with the information of each reference changeover pattern, the switching controller 171 outputs a changeover control signal to each of relevant ones of the switches SW1 to SW8 for shifting to the position 1 or 2 of the output terminal so that the relevant switches are each changed over. The reference changeover pattern for each switch contains the position 1 ("1" in FIG. 12) or the position 2 ("2" in FIG. 12) of the output terminal of the switch to be connected. "No Care" in FIG. 12 means, as described above, that no control information is contained in the relevant box.

When the treatment room data (No. 1) is inputted to the switching controller 171 from the CPU 131 in the electromagnet power supply controller 130, the switching controller 171 refers to the memory 172 and reads the corresponding switch changeover pattern (changeover pattern for the switch numbers 1 to 8 corresponding to the treatment room No. 1). In accordance with the information of the reference changeover pattern, the switching controller 171 performs the changeover operations of the relevant switches. Because the reference changeover pattern for the treatment room No. 1 (the selected treatment room 2A) has the switch numbers 1 to 8 being all "1", the switches SW1 to SW8 are all connected to their output terminals 1. As a result, respective currents are supplied from the switching power sources 162-1, 162-2, 162-3 and 162-4 to the switching electromagnet 6A and the bending electromagnets 21A, 23A, 25A and 26A which are arranged along the beam path 62. The supply of the currents to those electromagnets is realized by cooperation of the switching power source 160 and the switch yard controller 170.

Another example of the switch yard will be described with reference to FIG. 19. The switch yard of this example includes four switches. The same electromagnets as those in the switch yard 180 described above are connected to output terminals 1 and 2 of switches SW1, SW2. The bending electromagnets 23A, 25A and 26A are connected in series to an output terminal 1 of a switch SW4. The bending electromagnets 23B, 25B and 26B are connected in series to an output terminal 2 of the switch SW4. The bending electromagnets 23C, 25C and 26C are connected in series to an output terminal 2 of the switch SW3. The reference changeover patterns used in this example correspond to those shown in FIG. 12 for the Nos. 1 to 4 switches. The switch yard of this example includes smaller numbers of switches and power sources than the switch yard 180. Therefore, the construction of the proton beam therapy system can be simplified.

The control based on the control command data outputted from the CPU 101 is executed, as described above, under cooperation of the accelerator power supply 140, the beam path power supply 150, the switching power supply 160, and the switch yard controller 170. Such control actuates excitation of all the electromagnets arranged in the charged particle beam generator 1 and of all the electromagnets arranged in the beam paths 61 and 62 upstream and downstream of the junction between both the beam paths, which are required for introducing the ion beam to the selected treatment room, specifically the selected treatment room 2A.

Detectors (e.g., known limit switches) for detecting the changeover status of the corresponding switches are associated with the respective output terminals of the switches SW1 to SW8 in the switch yard 180. More specifically, a limit switch L11 is associated with one output terminal 1 of the switch SW1, and a limit switch L12 is associated with the other output terminal 2 of the switch SW1. Likewise, limit switches L21, L22, L31, L32, L41, L42, L51, L52, L61, L62, L71, L72, L81 and L82 are associated with the corresponding output terminals of the other switches, as shown in FIG. 11.

The determining unit 173 receives output signals from those limit switches and determines whether the actual changeover pattern (actual configuration data) provided in accordance with the output signals is identical to the reference changeover pattern (beam path configuration data) shown in FIG. 12. This determination means confirmation that the actual changeover pattern is matched with the reference changeover pattern. If the actual changeover pattern is matched with the reference changeover pattern, "OK" is outputted to the CPU 131 in the electromagnet power supply controller 130, and if not so, "NG" is outputted to it (as described in more detail later). Also, based on the detected signals regarding the switches SW1 to SW8, the determining unit 173 accesses the memory 172 to refer to the information of the reference changeover patterns stored therein, and determines which one (No.) of the treatment rooms 2A to 2C and 3 corresponds to the actual changeover condition of the switches SW1 to SW8. Thereafter, the determining unit 173 outputs a signal (actual treatment room information) representing a result of the determination to the CPU 131 in the electromagnet power supply controller 130.

The CPU 131 in the electromagnet power supply controller 130 collects, as actual status data (element status information) of the corresponding electromagnets, the actual current values inputted to the input/output conversion controller 132 from the ACR's 141a of the constant current controllers 141 in the accelerator power supply 140, the actual current values inputted to the input/output conversion controller 133 from the ACR's 151a of the constant current controllers 151 in the beam path power supply 150, and the actual current values inputted to the input/output conversion controller 134 from the ACR's 161a of the constant current controllers 161 in the switching power supply 160, followed by outputting the collected actual status data to the determining unit (information confirming unit) 104 in the central control system 100. The determination result (also called determination information or confirmation information) outputted from the determining unit 173 in the switch yard controller 170 is also outputted to the determining unit 104 through the CPU 131.

Thus, the determining unit 104 receives not only the actual status data (actual current value) representing the actual status of the electromagnet for each of the above-described units in the accelerator power supply 140, the beam path power supply 150, and the switching power supply 160, but also the actual status data of each corresponding electromagnet from the switch yard controller 170 (for example, the current value (actual current value) supplied from the switching power source 162, e.g., the switching power source 162-1, to the corresponding electromagnet). On the other hand, as described above, the determining unit 104 further receives the control command data (including the treatment room number data) prepared by the CPU 101. Then, the determining unit 104 compares the control command data with the electromagnet actual status data and compares the treatment room number data contained in the control command data with the treatment room information.

Another major feature of this embodiment resides in a manner of confirming the data in the determining unit 104. The manner will be described below with reference to FIG. 13 and FIG. 14.

Figure 13:
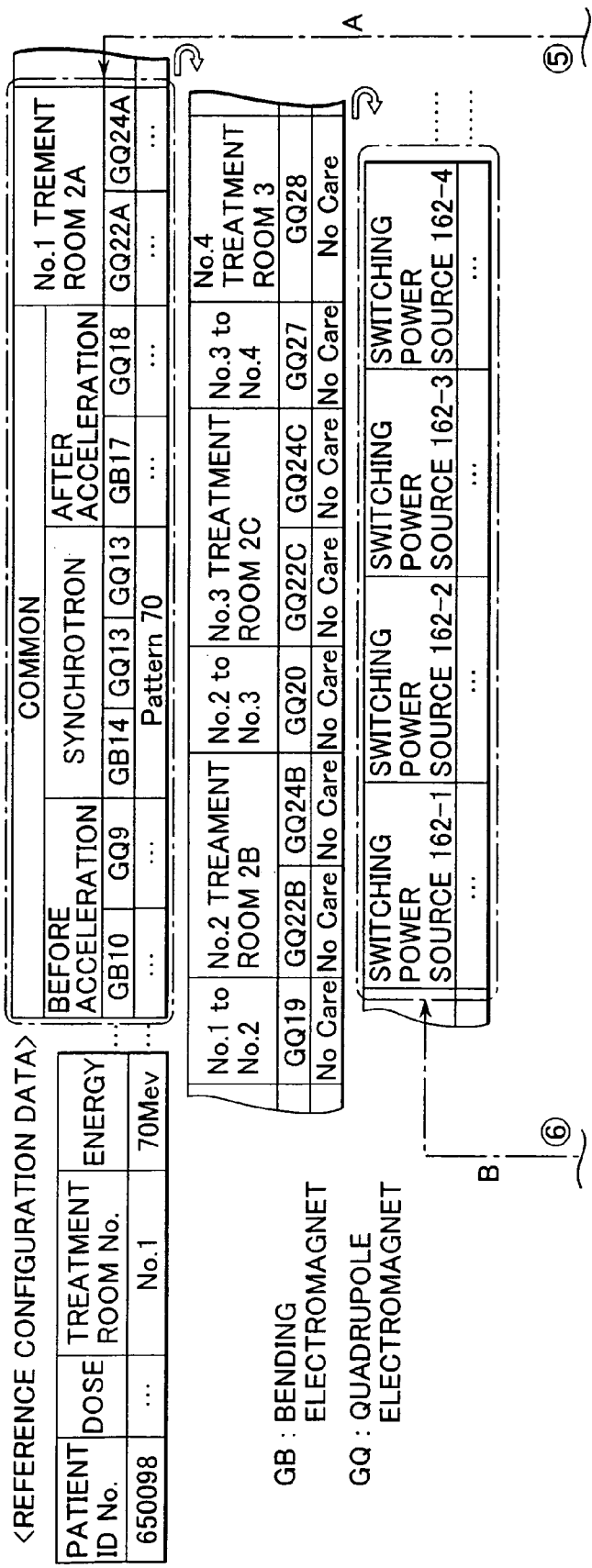
FIG. 13 is an upper half of representation of data comparison for explaining how data is compared in a determining unit.
Figure 14:
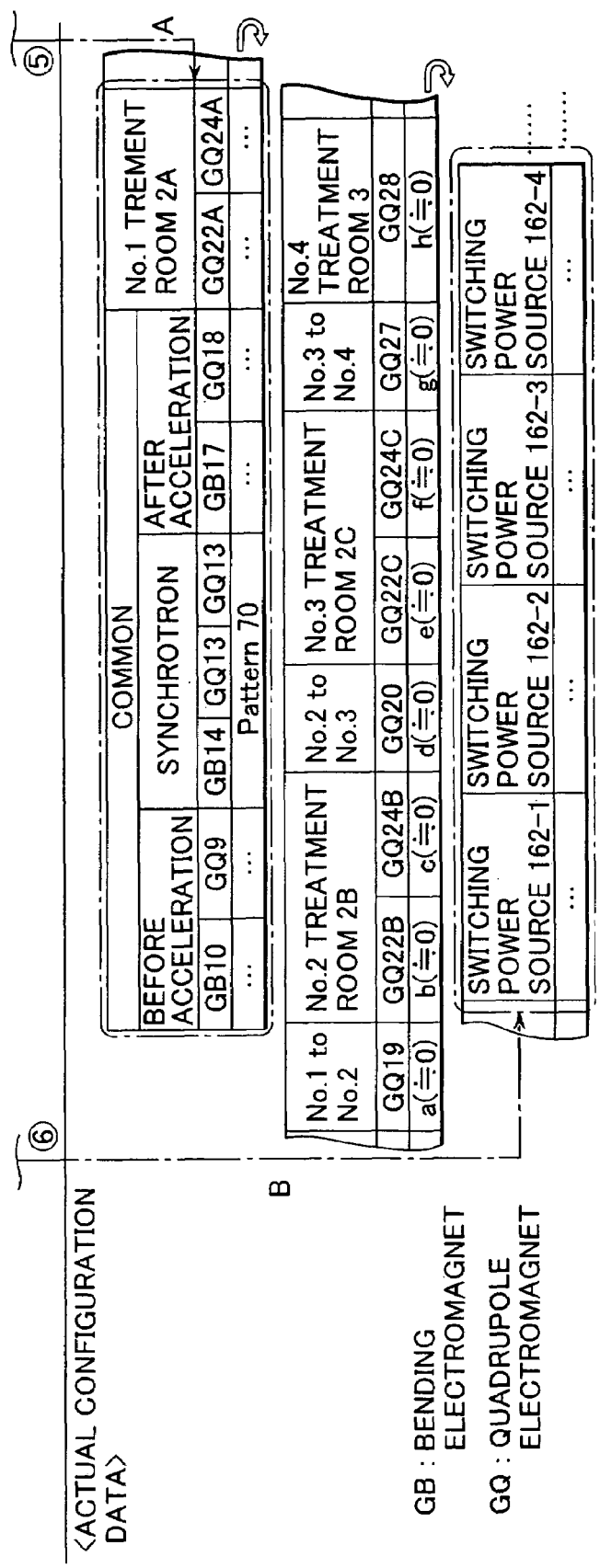
FIG. 14 is a lower half of representation of data comparison for explaining how data is compared in a determining unit.

FIG. 13 and FIG. 14 is a representation of data comparison for explaining how the data is confirmed in the determining unit 104. Data shown in FIG. 13 is the same as that shown in FIG. 10 as one example of the control command data, and data shown in FIG. 14 represents the corresponding electromagnet actual status data.

In FIG. 13 and FIG. 14, as described above, the control command data prepared by the CPU 101 contains the addresses assigned to all of the electromagnets for communication as control data, but those electromagnets, which do not directly take part in forming the beam path corresponding to the treatment room number as the irradiation target, are not positively controlled (namely the addresses are assigned to those electromagnets for communication as control data, but numerical values of the corresponding data are indefinite).

On the other hand, the electromagnet actual status data always contains, as numerical value data, the actual status data (current values detected by the ammeters) regarding all of electromagnets (as denoted by a, b, c, d, e, etc. in FIG. 14) regardless of whether the corresponding electromagnets have been actually controlled.

In consideration of the above-described actual background in the process of data generation, when comparing the control command data with the actual status data regarding the purpose of confirming the operation of the overall system, those data regarding the electromagnets not positively controlled are excluded from the comparison target in this embodiment. Specifically, the electromagnet actual status data regarding the electromagnets having been actually controlled (in the case of the treatment room 2A being selected, all the electromagnets arranged in the charged particle beam generator 1 and all the electromagnets arranged in the beam paths 61 and 62 upstream and downstream of the junction between both the beam paths) is extracted from among all the electromagnet actual status data. This extraction is executed by the determining-unit 104 selecting, from among all the electromagnet actual status data, those data corresponding to the electromagnets having control information in their control command data (i.e., all the electromagnets corresponding to sections A and B of the reference configuration data prepared by the CPU 101 shown in FIG. 13). That reference configuration data is the control command data. As a result, the electromagnet actual status data shown in the sections A and B in FIG. 13 and FIG. 14 is selected from among all the electromagnet actual status data shown in FIG. 14. The determining unit 104 compares the selected electromagnet actual status data with the control command data prepared by the CPU 101, i.e., those of the control command data in the sections A and B in FIG. 13 and FIG. 14, and checks whether the former electromagnet actual status data is matched with the latter control command data, thereby confirming the status of the control instructed by the CPU 101 for the overall system. When the determining unit 104 confirms that all the electromagnet actual status data is normal, it outputs an authorization signal for the overall system to the AND circuit 122 of the central interlock system 120 (see FIG. 4).

Eventually, the determining unit 104 in this embodiment extracts only the electromagnet actual status data regarding the treatment room selected to carry out the irradiation treatment therein, and compares the selected data with the control command data corresponding to the selected treatment room. Therefore, even when, by way of example, a trouble occurs in any one of the plural treatment rooms and the electromagnet actual status data regarding the relevant treatment room contains data other than an ordinary value, selection of the electromagnet actual status data to exclude the relevant treatment room from actual use for the treatment enables the means for extracting and determining data to reliably fulfill the intended role, i.e., the comparison between a command value and an actual value, without being affected by a detected signal having such an unordinary value. As a result, even in the case of a trouble occurring in one of the treatment rooms, the treatment operation can be continued by using the remaining normal treatment rooms. It is hence possible to prevent or minimize reduction of the treatment capability and to smoothly continue the treatment. In other words, a durable therapy system can be realized which undergoes less reduction of the treatment capability in the event of a trouble.

Still another major feature of this embodiment resides in opening/closing control of the above-mentioned shutters 7A, 7B, 7C, 7D and 8. This feature will be described in more detail.

Figure 15:
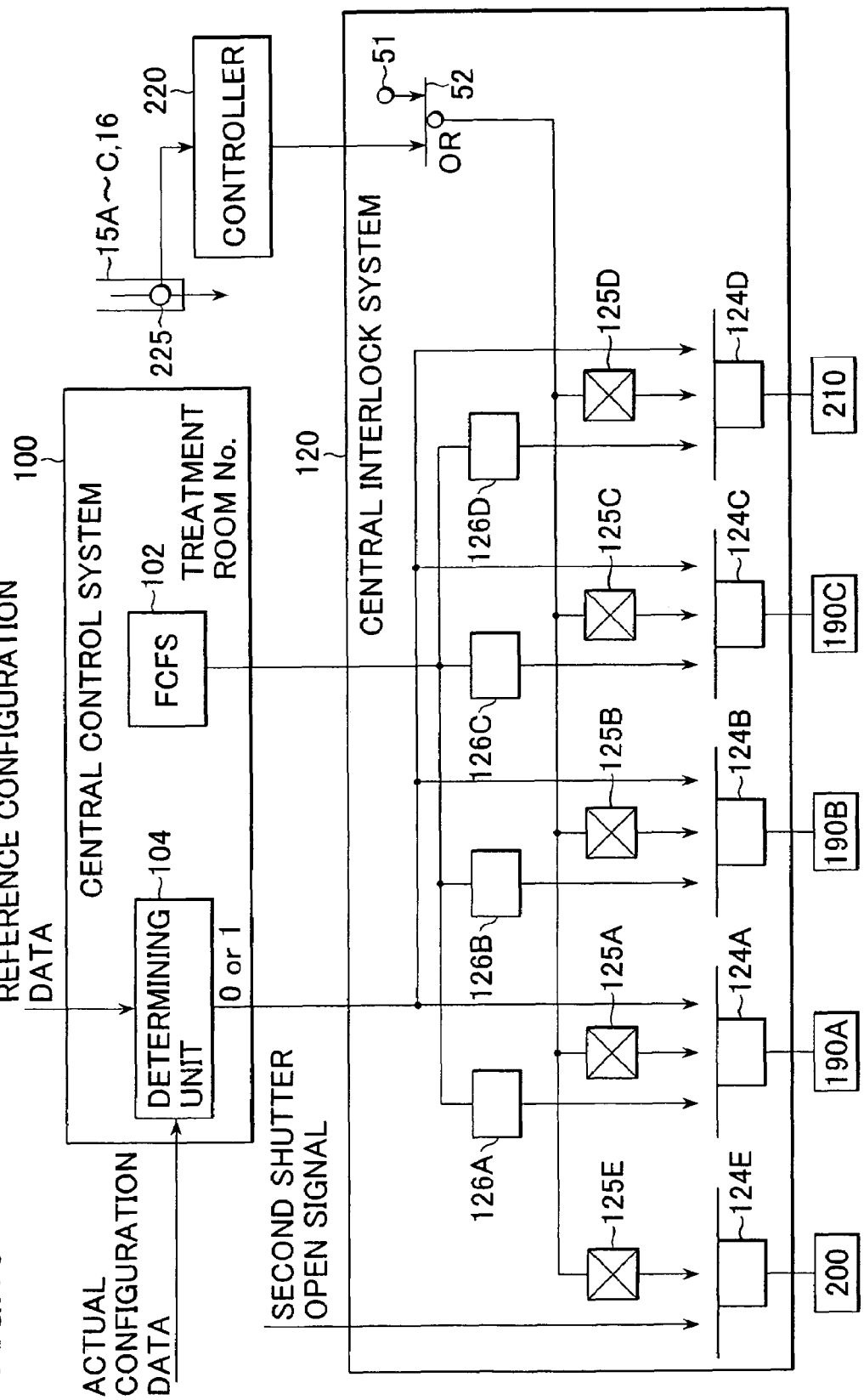
FIG. 15 is a block diagram showing the function of a central interlock system in relation to opening/closing control of shutters.

The opening/closing control of the above-mentioned shutters 7A, 7B, 7C, 7D and 8 is performed by the central interlock system 120. FIG. 15 is a block diagram showing the function of the central interlock system 120 in relation to the opening/closing control of those shutters.

As shown in FIG. 15, in addition to the AND circuits 121A-121C, 122 and 123 mentioned above, the central interlock system 120 further comprises five AND circuits 124A, 124B, 124C, 124D and 124E, NOT circuits 125A, 125B, 125C, 125D and 125E connected respectively to those AND circuits, and four signal output units 126A, 126B, 126C and 126D connected respectively to the four AND circuits 124A to 124D among the five AND circuits 124A to 124E.

The AND circuit 124A serves to output a driving control signal to the shutter driver 190A for opening and closing the shutter 7A provided in the second beam transport system 5A (the shutter is opened when the signal is "1", i.e., "ON"), and it is connected to the NOT circuit 125A and the signal output unit 126A. In other words, the AND circuit 124A, the NOT circuit 125A, and the signal output unit 126A constitute one group corresponding to the treatment room 2A. Similarly, the AND circuit 124B, the NOT circuit 125B, and the signal output unit 126B are associated with the treatment room 2B and cooperatively output a driving control signal to the shutter driver 190B for opening and closing the shutter 7B provided in the second beam transport system 5B. The AND circuit 124C, the NOT circuit 125C, and the signal output unit 126C are associated with the treatment room 2C and cooperatively output a driving control signal to the shutter driver 190C for opening and closing the shutter 7C provided in the second beam transport system 5C. The AND circuit 124D, the NOT circuit 125D, and the signal output unit 126D are associated with the treatment room 3 and cooperatively output a driving control signal to the shutter driver 210 for opening and closing the shutter 7D provided in the second beam transport system 5D. The AND circuit 124E is connected to the NOT circuit 125E and outputs a driving control signal to the shutter driver 200 for opening and closing the shutter 8 provided in the first beam transport system 4.

As described above, when the determining unit 104 in the central control system 100 compares the control data included in the control command data with the corresponding electromagnet actual status data and confirms that the operation is normal, it outputs the authorization signal for the overall system. This authorization signal is first inputted, as an ON signal "1", to each of the AND circuits 124A to 124D. At this time, respective signals from the signal output units 126A to 126D are also inputted to the AND circuits 124A to 124D. Further, a signal representing the treatment room number and outputted from the First Come First Serve 102 is inputted to the signal output units 126A to 126D. Then, each of the signal output units 126A to 126D outputs the ON signal "1" only when the treatment room number, which is the same as the treatment room number related to the relevant signal output unit, is inputted from the First Come First Serve 102 as described above, and it outputs an OFF signal "0" if otherwise. As a result, if the treatment room number inputted from the First Come First Serve 102 is 1 (which means selection of the treatment room 2A), only an output from the signal output unit 126A becomes an ON signal "1" and outputs of the other signal output units 126B to 126D become each an OFF signal "0". At this time, a signal from a separately provided dose detection controller 220 is also inputted to the AND circuits 124A to 124D through the corresponding NOT circuits 125A to 125D. This signal is usually, as described later, an ON signal "1" with the presence of the NOT circuits 125A to 125D. Accordingly, an ON signal "1" is outputted from the AND circuit 124A corresponding to the signal output unit 126A, whereby only the shutter 7A provided in the second beam transport system 5A extended into the treatment room 2A is controlled to be open while the other shutters 7B, 7C and 7D are held closed. Stated another way, the other second beam transport systems 5B, 5C and 5D are shut off by the shutters 7B, 7C and 7D, while only the beam path communicating with the treatment room 2A is opened. Likewise, if the treatment room number inputted from the First Come First Serve 102 is 2, 3 or 4, only an output from the signal output unit 126B, 126C or 126D becomes an ON signal "1" and the corresponding shutter 7B, 7C or 7D is controlled to be open and only the beam path communicating with the corresponding treatment room 2B, 2C or 3 is opened.

In this respect, the shutters 7A, 7B, 7C and 7D are provided with not-shown open/close detectors (e.g., known limit switches), and respective detected signals are inputted to the central interlock system 120 for comparison with the corresponding command signals.

Figure 16:
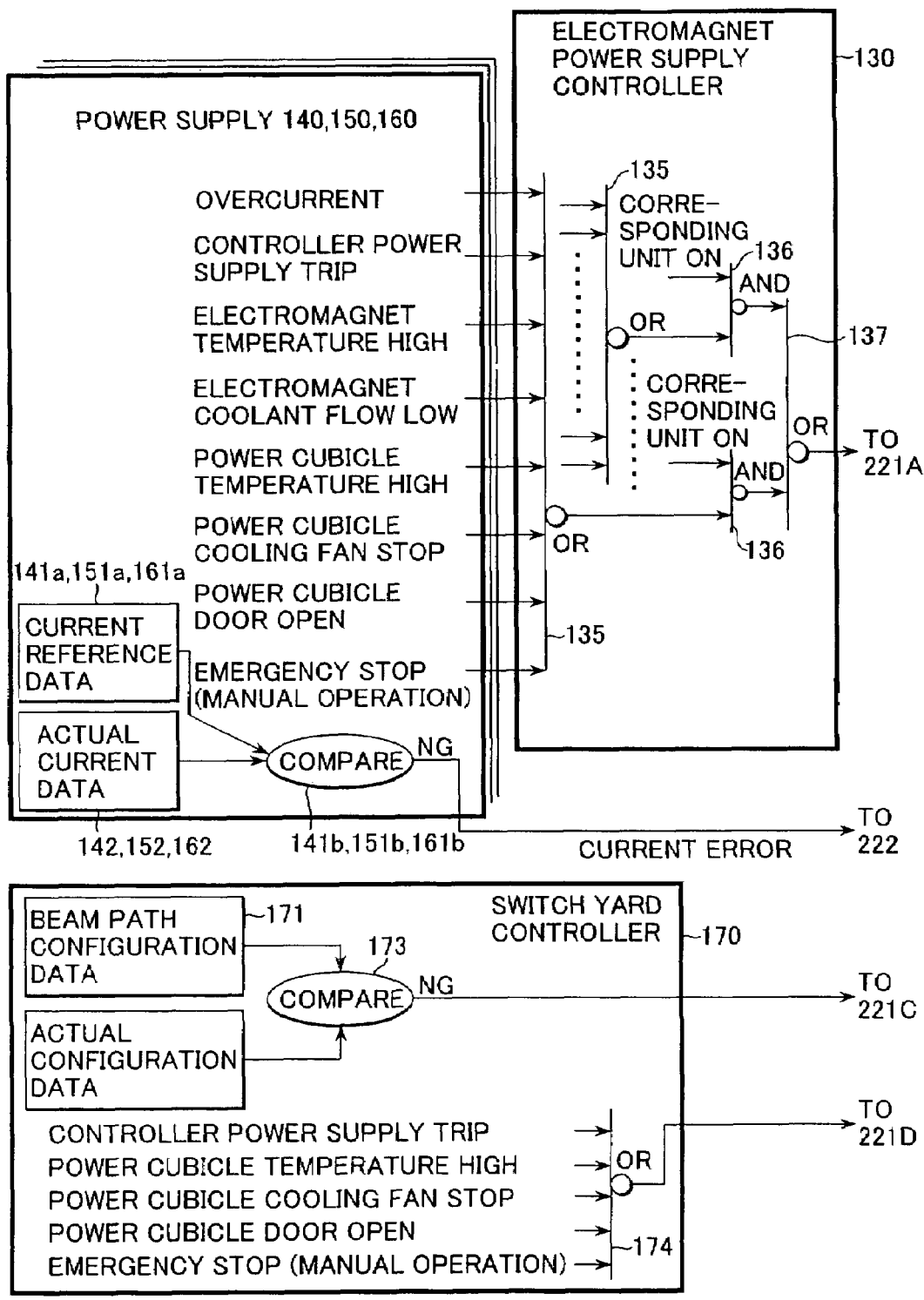
FIG. 16 is an explanatory view showing the interlock functions of an electromagnet power supply controller and the switch yard controller.
Figure 17:
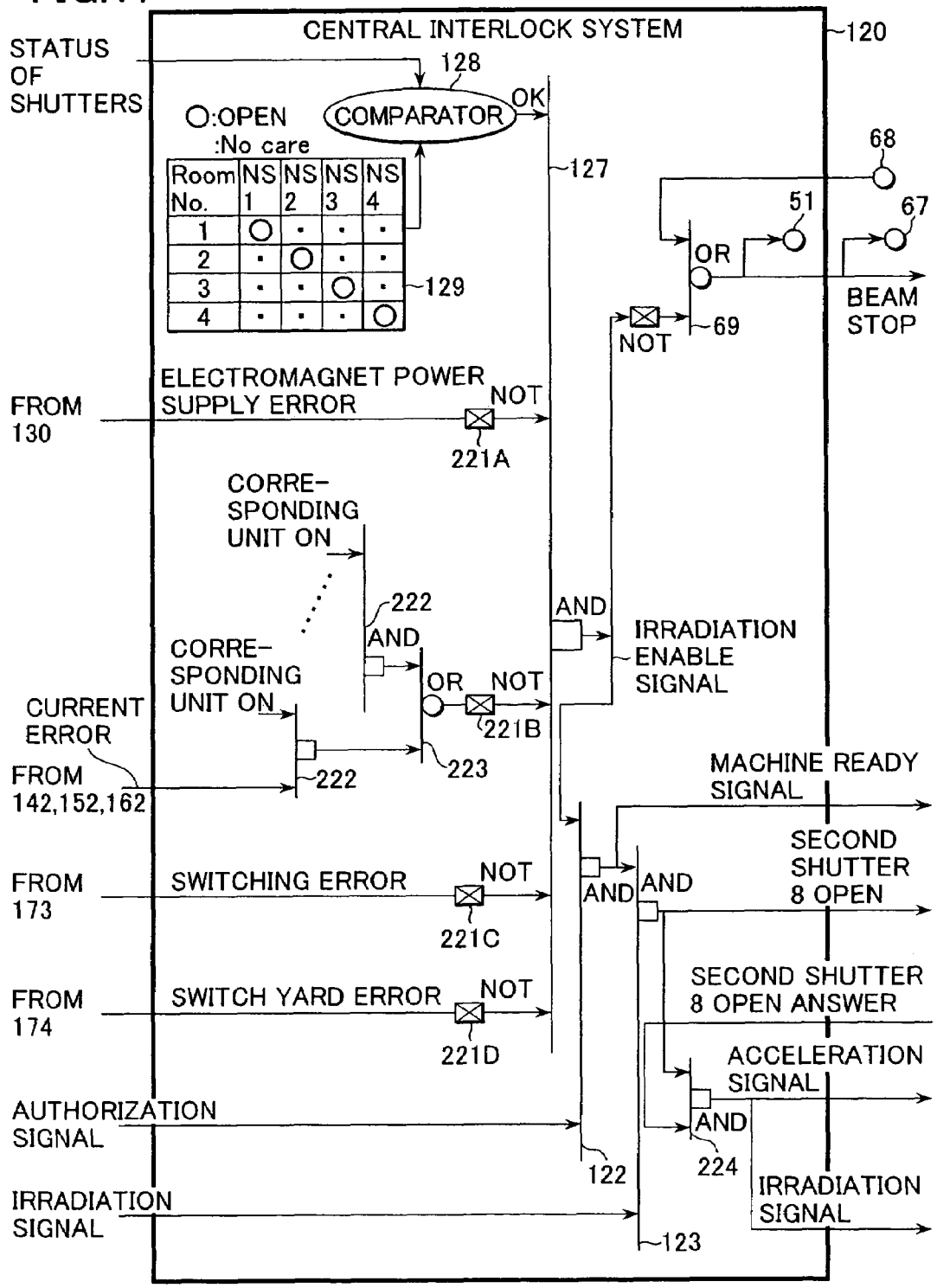
FIG. 17 is a block diagram showing another function (lock function in the event of error detection) of the central interlock system, including the shutter opening/closing comparison function.

FIG. 16 is an explanatory view showing the interlock functions of the electromagnet power supply controller and the switch yard controller, and FIG. 17 is a block diagram showing another function (lock function in the event of error detection) of the central interlock system, including the shutter opening/closing comparison function. Note that the components already described above are denoted by the same symbols and a description of those components is omitted here.

As shown in FIG. 17, the central interlock system 120 includes a main AND circuit 127 taking part in the lock function in the event of error (abnormality) detection. One of signals inputted to the AND circuit 127 is an output signal from a comparator 128 taking part in the shutter opening/closing operation. The comparator 128 receives the shutter open/close detection signals (actual shutter operation information, i.e., respective statuses of the switches) from the above-described limit switches, for example, and the command signals outputted, as described above with reference to FIG. 15, from the AND circuits 124A to 124D of the central interlock system 120 to the shutter drivers 190A to 190C and 210 for driving the shutters 7A to 7D. At this time, however, among the command signals, only the shutter opening command signal supplied to the relevant one of the shutters 7A to 7D, which is driven to be open, is extracted by not-shown extracting means and inputted to the comparator 128, whereas the command signals supplied to the other shutters held in the closed state are not inputted to the comparator 128 (see a table 129 in FIG. 17). When the shutter supplied with the opening command signal has operated to normally open, the comparison (determination) made in the comparator 128 is satisfied, and an ON signal "1" is inputted to the AND circuit 127.

In addition the above-mentioned signal regarding the shutter operation, the AND circuit 127 receives other four signals regarding an "electromagnet power supply error", "current error", "switching error", and "switch yard error". These four signals will be described below one by one.

(1) Electromagnet Power Supply Error Signal

The accelerator power supply 140, the beam path power supply 150, and the switching power supply 160 are provided with various error (abnormality) detecting means (not shown) for each of the above-mentioned units (each unit comprising the constant current controller, the power source, and the ammeter). In the event of error detection, a resulting detected signal is outputted to corresponding one of the input/output conversion controllers 132, 133 and 134 in the electromagnet power supply controller 130. Examples of errors to be detected include an overcurrent in the power supply, a power supply trip in the constant current controller, high temperature (overheating) of the electromagnet at the current supply designation, a low flow of a cooling fluid (air or another coolant) supplied to the electromagnet, high temperature (overheating) of a power cubicle, stop of a fan for cooling the power cubicle, and a door open state of the power cubicle. In addition, a signal generated upon manual operation of an emergency stop switch (not shown) provided for each unit is also inputted to corresponding one of the input/output conversion controllers 132, 133 and 134.

The error signals (including the emergency switch input signal; this is similarly applied to the following description) from the relevant units in the power supplies 140, 150 and 160 are collected into the CPU 131 (see FIG. 4) through the input/output conversion controllers 132, 133 and 134 in the electromagnet power supply controller 130. The CPU 131 has the function equivalent to the construction comprising sets of an OR circuit 135, an AND circuit 136 and another OR circuit 137, which are provided in the same number as the total number of the above-mentioned units (FIG. 16 shows that function in the form of a circuit and the CPU 131 may have such a circuit arrangement as hardware). The above-mentioned eight error signals from the relevant units are converted into one output signal through the OR circuit 135. In other words, if any one error is detected, the output signal from the OR circuit 135 becomes an ON signal "1". This output signal is inputted to one input terminal of the corresponding AND circuit 136. At the same time, the other input terminal of the AND circuit 136 receives an ON signal "1" when the corresponding unit is in the effective (positive) control state in accordance with the command. Accordingly, when the respective above-mentioned units in the power supplies 140, 150 and 160 are in the effective (positive) control state in accordance with the control command data, which is generated by the central control system 100, corresponding to the formation of the beam transport path upon selection of one of the treatment rooms 2A, 2B, 2C and 3, the error signal from the OR circuit 135 is outputted, as it is, to the OR circuit 137 in the final stage. On the other hand, when the unit is not in the effective (positive) control state (corresponding to "No Care" in the tables described above), an OFF signal "0" is outputted to the OR circuit 137 because even if the error signal is an ON signal "1", it is made invalid (ignored). In such a way, when any error occurs in any of the units in the power supplies 140, 150 and 160 under the effective control, an ON signal "1" representing an "electromagnet power supply error" is inputted to the central interlock system 120 from the OR circuit 137. In the central interlock system 120, the inputted ON signal "1" is applied to the AND circuit 127 through the NOT circuit 221A. Thus, in the absence of an error, an ON signal "1" is inputted to the AND circuit 127, while in the event of an error, an OFF signal "0" is inputted to it and an output signal from the AND circuit 127 also becomes an OFF signal "0" with certainty.

(2) Current Error Signal

As described above, the accelerator power supply 140, the beam path power supply 150, and the switching power supply 160 include the determining units 141b, 151b and 161b, respectively, for each of the above-mentioned units (each unit comprising the constant current controller, the power source, and the ammeter). The determining units 141b, 151b and 161b determine whether the corresponding power sources 142, 152 and 162 and ACR's 141a, 151a and 161a function normally without errors (for example, whether the confirmation result is within a predetermined range). In the event of error determination, a resulting signal (NG signal) is inputted, as an ON signal "1" representing a "current error", to the central interlock system 120. The central interlock system 120 includes sets of an AND circuit 222 and one OR circuit 223, which are provided in the same number as the total number of the above-mentioned units. The signal representing the current error is inputted to one input terminal of the corresponding AND circuit 222. At the same time, similarly to the case of above (1), the other input terminal of the AND circuit 222 receives an ON signal "1" when the corresponding unit is under the effective (positive) control in accordance with the command. Accordingly, when the relevant unit is in the effective (positive) control state corresponding to selection of one of the treatment rooms 2A, 2B, 2C and 3, the current error signal is outputted, as it is, to the OR circuit 223 in the final stage. On the other hand, when the unit is not in the effective (positive) control state, an OFF signal "0" is outputted to the OR circuit 223. The thus-outputted signal is applied to the AND circuit 127 through a NOT circuit 221B. Hence, in the absence of a current error, an ON signal "1" is inputted to the AND circuit 127, while in the event of a current error, an OFF signal "0" is inputted to it and an output signal from the AND circuit 127 also becomes an OFF signal "0" with certainty.

(3) Switching Error Signal

As described above, the switch yard controller 170 includes the determining unit 173. The determining unit 173 makes comparison to determine whether the switches 1 to 8 and the switching controller 171 function normally without errors. In the event of error determination, a resulting signal (NG signal) is inputted, as an ON signal "1" representing a "switching error", to the central interlock system 120. In the central interlock system 120, the inputted signal is applied to the AND circuit 127 through a NOT circuit 221C. Hence, in the absence of a switching error, an ON signal "1" is inputted to the AND circuit 127, while in the event of a switching error, an OFF signal "0" is inputted to it and an output signal from the AND circuit 127 also becomes an OFF signal "0" with certainty.

(4) Switch Yard Error

The switch yard controller 170 includes, in addition to the determining unit 173, various error (abnormality) detecting means (not shown) regarding the switch yard 180 and the switch yard controller 170 itself. In the event of error detection, a resulting detected signal is outputted to a separately provided OR circuit 174. Examples of errors to be detected include a power supply trip in the switching controller 171, high temperature (overheating) of a power cubicle, stop of a fan for cooling the power cubicle, and a door open state of the power cubicle. In addition, a signal generated upon manual operation of an emergency stop switch (not shown) provided the switch yard controller 170 is also inputted to the OR circuit 174.

The above-mentioned five error signals are converted into one output signal through the OR circuit 174. In other words, if any one error is detected, the output signal from the OR circuit 174 becomes an ON signal "1".

In the central interlock system 120, the inputted ON signal "1" is applied to the AND circuit 127 through a NOT circuit 221D. Hence, in the absence of an error, an ON signal "1" is inputted to the AND circuit 127, while in the event of an error, an OFF signal "0" is inputted to it and an output signal from the AND circuit 127 also becomes an OFF signal "0" with certainty.

In such a way, when any error is not detected regarding "shutter operation", "electromagnetic force supply", "current", "switching", and "switch yard", an ON signal "1" is outputted, as an irradiation enable signal, from the AND circuit 127. This irradiation enable signal is inputted to the AND circuit 122 along with the above-described authorization signal from the determining unit 104 in the central control system 100. If the irradiation enable signal is inputted with no error detection in all the components under monitoring and the authorization signal is also inputted upon the substantial match of the control command data with the electromagnet actual status data as described above, the AND circuit 122 outputs an ON signal "1", as a signal (display signal) representing that the machine has been brought into a completely ready state, to the display 39 on the treatment console 37, and also outputs a similar signal to the AND circuit 123. In response to the display signal, the display 39 indicates that the machine is in the completely ready state (namely, displays a screen for finally confirming whether the irradiation is to be started). When the irradiation instruction switch (or button) 42 is operated, for example, by a doctor (or an operator in some foreign countries; in Japan, this person must be a doctor in conformity with legislative regulations from the standpoints of safety and humanity), a resulting irradiation start signal is inputted, as an ON signal "1", to one input terminal of the AND circuit 123 in the central interlock system 120. At this time, since an ON signal "1" serving as the machine ready signal is inputted to the other input terminal of the AND circuit 123 as described above, the AND circuit 123 outputs an ON signal "1" as a signal for actuating control to open the second shutter 8 provided in the first beam transport system 4.

Returning to FIG. 13, the second shutter open signal is inputted to one input terminal of the AND circuit 124E in the central interlock system 120, which is related to the second shutter 8. At this time, as described above, the signal inputted to the other input terminal of the AND circuit 124E from the dose detection controller 220 through the NOT circuit 125E is usually an ON signal "1". As a result, the AND circuit 124E outputs an ON signal "1", whereby the second shutter 8 provided in the first beam transport system 4 is controlled to be open. Similarly to the first group of shutters 7A to 7D described above, the second shutter 8 is provided with a not-shown open/close detecting means (e.g., a known limit switch). Then, upon the second shutter 8 being opened, a resulting detected signal (second shutter open detection signal) is inputted to one input terminal of an AND circuit 224 separately disposed in the central interlock system 120. At this time, since an ON signal "1" serving as the second shutter open signal is inputted to the other input terminal of the AND circuit 224, the AND circuit 224 outputs an ON signal "1" as an irradiation (emission) signal and an acceleration signal, which are supplied respectively to the linac 11 and the high-frequency acceleration cavity in the synchrotron 12.

Thus, the ion beam emitted from the charged particle beam generator 1 is accelerated by the synchrotron 12, and the ion beam exiting from the synchrotron 12 is transported through the first beam transport system 4 while passing the second shutter 8 in the open state. Then, the ion beam is introduced to one of the second beam transport systems 5A to 5D corresponding to one of the treatment rooms 2A to 2C and 3, in each of which the patient as the irradiation target is present, while passing one of the first shutters 7A to 7D in the open state. Thereafter, the ion beam is irradiated to the tumor in the body of the patient 30 in an optimum condition in accordance with the treatment plan through one of the irradiation units 15A to 15C and 16 in the treatment rooms 2A to 2C and 3.

In this respect, as shown in FIG. 13, known dosimeters (dose detecting means or accumulated dose detecting means) 225 are provided in respective nozzles of the irradiation units 15A to 15C and 16, and resulting detected signals are inputted to the dose detection controller 220. The dose detection controller 220 usually outputs an OFF signal "0". Then, when the accumulated dose detected by the dosimeters 225 reaches a predetermined value (that may be a stored preset value or may be given by reading the value in the treatment plan per patient (see the column "dose" in the patient data shown in FIG. 7) through the CPU 101 in the central control system 100 each time the irradiation is started), the dose detection controller 220 outputs an ON signal "1". Accordingly, OFF signals "0" are inputted to all the AND circuits 124A to 124E through the respective NOT circuits 125A to 125E. As a result, the first shutters 7A to 7D, which have been so far opened, are controlled to be closed through the shutter drivers 190A to 190C and 210. Likewise, the second shutter 8, which has been so far opened, is automatically closed through the shutter driver 200. An output of the AND circuit 127 is outputted from the OR circuit 69 through a NOT circuit. This output serves as the beam stop signal. One or more of the shutters 7A to 7D, which are still open, are closed by the beam stop signal that is applied from an OR circuit 52, shown in FIG. 13, to relevant one or more of the AND circuits 124A, 124B, 124C, 124D and 124E through a terminal 51 and relevant one or more of the NOT circuits 125A, 125B, 125C, 125D and 125E. This ensures that, when any error (abnormality) occurs in the proton beam therapy system and the beam stop signal is outputted from the central interlock system 120, i.e., from the OR circuit 69, any shutter being still open is reliably closed. Thus, safety in the proton beam therapy system can be remarkably improved.

FIG. 18 shows a flow of the above-mentioned process with time. Note that, because the second shutter 8 is lighter than each of the first shutters 7A to 7D, it is constructed as one capable of being quickly moved in a shorter time for the opening/closing operation (particularly for the opening operation).

The particle beam therapy system of this embodiment, having the construction described above, can provide the following advantages.

In this embodiment, the first shutters 7A to 7D for shutting off the beam path are provided respectively in the second beam transport systems 5A to 5D. Stated another way, to prevent the beam from being erroneously transported to the treatment room that is not the irradiation target, the shutters 7A to 7D for physically blocking the beam itself are disposed in the respective beam paths. Therefore, safety can be improved in comparison with the related art resorting to only reliability of software used in an electromagnet switching controller.

In this embodiment, the CPU 101 in the central control system 100 forms the control command data per patient by employing the patient identification information (ID No.), the treatment room information, and the treatment plan information of each patient. Therefore, the doctor side is just required to prepare only the treatment plan information for each patient, and the operator side is just required to input only the patient identification information and the treatment room information, both representing who is present as the patient in which one of the treatment rooms, to the CPU 101 from the patient ID input device 43. Based on the treatment plan information, the patient identification information, and the treatment room information, the CPU 101 automatically forms the control command data per patient. As a result, when forming the final control command data per patient, it is no longer required to prepare a large amount of data covering all of the treatment plan information for each patient set from the medical point of view and the information necessary for operating the therapy system. Thus, since work for preparing data can be separately allocated to the doctor side and the operator side, the system construction can be simplified and the treatment can be smoothly conducted at higher efficiency.

In this embodiment, the beam transport path is controlled by the First Come First Serve 102 such that the ion beam is transported with higher priority to the treatment room in which the patient has been brought into an irradiation ready state at earlier timing. It is therefore possible to freely start preparations for irradiation to the patients in the plural treatment rooms 2A to 2C and 3 as appropriate, and to carry out the irradiation of the ion beam in sequence from the treatment room in which the preparations for irradiation have been completed. In other words, unlike the case of, for example, presetting the irradiation sequence for the respective treatment rooms and transporting the ion beam in accordance with the preset sequence, the treatment room in which the preparations for irradiation are lasting for a longer time or the patient's feeling has worsened, for example, can be automatically put off after the treatment room in which the patient has already been brought into an irradiation ready state at that time. With such flexibility, a wasteful waiting time can be reduced and the therapy system can be utilized at maximum efficiency. Hence, treatment can be smoothly conducted on a larger number of patients at higher efficiency. Other advantages reside in that presetting of the irradiation sequence and schedule is not always required, and the schedule can be flexibly changed with ease. This means that the time and labor required for the operator during the treatment can be reduced to a large extent.

In this embodiment, when the CPU 101 forms the control command data per treatment room depending on selection of one of the treatment rooms 2A to 2C and 3 and the electromagnets are operated in accordance with the formed control command data, the detected signals from the ammeters 143, 153 and 163, etc. associated with the electromagnets are outputted regardless of which one of the treatment rooms has been selected. Then, the electromagnet actual status data is obtained from the detected signals, and the determining unit 104 extracts and compares those of the electromagnet actual status data regarding the selected treatment room with the control command data per treatment room provided from the CPU 101, thereby determining a match between them. Stated another way, the determining unit 104 finally extracts only the data regarding one of the treatment rooms 2A to 2C and 3, which has been selected to carry out the irradiation treatment therein, and compares the selected data with the corresponding control command data per treatment room. Therefore, even when, by way of example, a trouble occurs in any one of the treatment rooms 2A to 2C and 3 and data other than an ordinary value is detected as the electromagnet actual status data regarding the relevant treatment room, selection of the electromagnet actual status data to exclude the relevant treatment room from actual use for the treatment enables the determining unit 104 to reliably fulfill the intended role, i.e., the comparison between a command value and an actual value, without being affected by a detected signal having such an unordinary value. As a result, even in the case of a trouble occurring in one of the treatment rooms, the treatment operation can be continued by using the remaining normal treatment rooms. It is hence possible to prevent or minimize reduction of the treatment capability and to smoothly continue the treatment. In other words, a durable therapy system can be realized which undergoes less reduction of the treatment capability in the event of a trouble.

In this embodiment, the switches 1 to 8 of the switch yard 180 are connected such that, when electric power from the above-mentioned four power sources 162-1 to 162-4 is supplied to two or more of three systems, i.e., a system (including the bending electromagnets 6A, 21A, 23A, 25A and 26A) related to the second beam transport system 5A, a system (including the bending electromagnets 6B, 21B, 23B, 25B and 26B) related to the second beam transport system 5B, and a system (including the bending electromagnets 6C, 21C, 23C, 25C and 26C) related to the second beam transport system 5C, any beam transport path is not formed in the second beam transport systems 5A to 5C (namely, when any one beam transport path is established, electric power is always supplied to only the group of electromagnets in one system corresponding to the established path).

With such an arrangement, in a normal condition, electric power is supplied to only one electromagnets group system to establish one beam transport path so that the beam is introduced to only the treatment room in which the irradiation is to be carried out. On the other hand, if electric power is supplied to the plural electromagnet group systems at the same time because of any error, no beam transport paths are formed and the beam is not introduced to all of the treatment rooms 2A to 2C and 3. Thus, it is possible to reliably prevent the beam from being erroneously introduced to the treatment room in which the irradiation is not scheduled at that time, and hence to improve safety.

Further, in this embodiment, when the patient ready switch 38 is operated to input a signal indicating the patient in the irradiation ready state, the display 39 displays that the preparations for the irradiation in the charged particle beam generator 1 and the beam transport systems 4 and 5A to 5D have been completed. Responsively, an instruction for the start of the irradiation is inputted through the irradiation instruction switch 42.

Accordingly, whether to start the irradiation or not can be decided on in one of the treatment rooms 2A to 2D and 3 (or in the irradiation control room 33 near the relevant treatment room) until a point in time immediately before the irradiation is actually started subsequent to the completion of the preparations on the machine side after the completion of the preparations for irradiation on the patient side. As a result, the irradiation can be canceled in a flexible way at any point in time until just before the start of the irradiation, taking into account, for example, that the patient's condition and feeling are in a state sufficiently allowable to receive the irradiation treatment, that the patient's feeling is not worsened, or that the patient does not want to go to the toilet. Hence, the irradiation treatment can be performed on each patient in a safe and prudent manner without problems.

Additionally, in the embodiment described above, when the determining unit 173 in the switch yard controller 170 determines based on the detected signals from the switches 1 to 8 which one of the treatment rooms 2A to 2C and 3 corresponds to the actual changeover status of the switches 1 to 8, the actual treatment room information is obtained by accessing the memory 172 and referring to the table stored in it. However, the present invention is not limited to that embodiment. The equivalent function may be provided, instead of such software processing, by using a hardware configuration (e.g., a combination of many logical circuits).

According to the present invention, treatment using a charged particle beam can be performed on patients in a safe and prudent manner without problems.

What is claimed is:

1. A particle beam therapy system comprising:
   a charged particle beam generator for emitting a charged particle beam;
   a plurality of irradiation units disposed in a plurality of treatment rooms, respectively, for irradiating the charged particle beam therein;
   a plurality of beam transport systems in communication with said charged particle beam generator and transporting the charged particle beam emitted from said charged particle beam generator separately to respective said plurality of irradiation units in said plurality of treatment rooms;
   first manual input devices provided respectively in said plurality of treatment rooms or a plurality, of control rooms formed corresponding to said plurality of treatment rooms for generating irradiation ready signals;
   a treatment sequence deciding unit for deciding a sequence of introducing the charge particle beam to said plurality of treatment rooms in an order in which the irradiation ready signals have been outputted from said first manual input devices, and outputting treatment room information representing a selected treatment room with top priority, to which the charged particle beam is to be first introduced;
   a preparation confirming unit for confirming that preparation for generation of the charged particle beam in said charged particle beam generator are completed and preparation for transport of the charged particle beam in the plurality of beam transport systems for introducing the charged particle beam to one of the plurality of irradiation units in the selected treatment room with top priority which said treatment room information from said treatment sequence deciding unit represents, followed by outputting machine ready information;
   a display unit device for displaying the machine ready information for the irradiation unit in the selected treatment room with top priority;

a second manual input device provided in each of said plurality of treatment rooms or each of said plurality of control rooms, and generating an irradiation start signal; and an emission start controller for outputting an emission start signal based on said machine ready information and said irradiation start signal outputted from said second manual input device in the selected treatment room with top priority.

2. A particle beam therapy system according to claim 1, wherein said first manual input device and said second manual input device comprise separate control buttons or switches disposed in positions different from each other.

3. A particle beam therapy system according to claim 1, further comprising:

first element groups disposed respectively in said plurality of beam transport systems, and a second element group disposed in said charged particle beam generator;

a control information forming unit for forming control command information, which includes control information for the first element group in the plurality of beam transport systems for introducing the charged particle beam to the selected treatment room and control information for said second element group, by using at least treatment room information representing the selected treatment room and treatment plan information specified depending on patient identification information; and an information confirming unit for selecting, from among element information including detected status information of said first element groups and detected status information of said second element group, the status information of the first element group in the plurality of beam transport systems extended into the selected treatment room and the status information of the second element group, and confirming that the selected status information is matched with control information for the relevant element groups, which is included in said control command information.

4. A particle beam irradiating method for irradiating a charged particle beam emitted from a charged particle beam generator to a patient in selected one of a plurality of treatment rooms by an irradiation unit in the selected treatment room, the irradiating method comprising the steps of:

deciding, based on irradiation ready signal outputted from first manual input devices provided respectively in said plurality of treatment rooms or a plurality of control rooms a sequence of introducing the charged particle beam to said plurality of treatment rooms in an order in which the irradiation ready signals have been outputted from said first manual input devices, and outputting treatment room information representing the selected treatment room with top priority, to which the charged particle beam is to be first introduced;

confirming that preparation for generation of the charged particle beam in said charged particle beam generator is completed and preparation for transport of the charged particle beam in a beam transport system for introducing the charged particle beam to the irradiation unit in the selected treatment room with top priority which said treatment room information from said treatment sequence deciding unit represents, followed by outputting machine ready information;

displaying the machine ready information for the irradiation unit in the selected treatment room with top priority or a corresponding control room, with a display unit device; and outputting an emission start signal based on said machine ready information and an irradiation start signal outputted from second manual input device in the selected treatment room with top priority or the corresponding control room.

* * * * *